(12) United States Patent
Banes

(10) Patent No.: US 6,645,759 B2
(45) Date of Patent: Nov. 11, 2003

(54) APPARATUS FOR GROWING CELLS IN CULTURE UNDER SHEAR STRESS AND/OR STRAIN

(75) Inventor: Albert J. Banes, Hillsborough, NC (US)

(73) Assignee: Flexcell International Corporation, McKeesport, PA (US)

( * ) Notice: Subject to any disclaimer, the term of this patent is extended or adjusted under 35 U.S.C. 154(b) by 267 days.

(21) Appl. No.: 09/733,017

(22) Filed: Dec. 8, 2000

(65) Prior Publication Data

US 2001/0003653 A1 Jun. 14, 2001

Related U.S. Application Data

(63) Continuation-in-part of application No. 09/454,327, filed on Dec. 3, 1999.
(60) Provisional application No. 60/111,023, filed on Dec. 4, 1998.

(51) Int. Cl.$^7$ ................................................. C12M 3/00
(52) U.S. Cl. ............................ 435/293.1; 435/294.1; 435/305.3
(58) Field of Search .......................... 435/289.1, 293.1, 435/294.1, 305.2, 305.3; 422/292, 295; 134/84, 88, 89, 92; 165/170, 172, 175, 176, DIG. 464, DIG. 465, DIG. 466

(56) References Cited

U.S. PATENT DOCUMENTS

| | | | |
|---|---|---|---|
| 2,521,475 A | * 9/1950 | Nickolas | 165/168 |
| 4,087,327 A | 5/1978 | Feder et al. | 195/1.7 |
| 4,228,243 A | * 10/1980 | Iizuka | 435/294.1 |
| 4,623,355 A | 11/1986 | Sawruk | 623/66 |
| 4,642,220 A | 2/1987 | Björkman | 422/101 |
| 4,695,547 A | 9/1987 | Hilliard et al. | 435/173 |
| 4,831,869 A | 5/1989 | Fowler et al. | 73/150 |
| 4,839,280 A | 6/1989 | Banes | 435/285 |
| 4,839,292 A | 6/1989 | Cremonese | 435/313 |
| 4,908,319 A | 3/1990 | Smyczek et al. | 435/285 |
| 4,940,853 A | 7/1990 | Vandenburgh | 435/240.23 |
| 5,240,854 A | * 8/1993 | Berry et al. | 435/305.1 |
| 5,273,905 A | 12/1993 | Muller et al. | 435/301 |
| 5,348,879 A | 9/1994 | Shapiro et al. | 435/240.241 |
| 5,414,556 A | 5/1995 | Focht | 359/398 |
| 5,843,766 A | 12/1998 | Applegate et al. | 435/284.1 |
| 5,958,760 A | 9/1999 | Freeman | 435/286.5 |
| 6,015,590 A | * 1/2000 | Suntola et al. | 427/255.23 |

FOREIGN PATENT DOCUMENTS

GB   2155948   10/1985   ............ C12M/1/18

OTHER PUBLICATIONS

Leung et al., "Cyclic Stretching Stimulates Synthesis of Matrix Components by Arterial Smooth Muscle Cells in Vitro", Science, vol. 191, Feb. 6, 1976, pp. 475–477.

(List continued on next page.)

*Primary Examiner*—William H. Beisner
(74) *Attorney, Agent, or Firm*—Webb Ziesenheim Logsdon Orkin & Hanson, P.C.

(57) ABSTRACT

Disclosed is a cell culture device for inducing shear stress and/or strain on cells. The device includes a cell culture membrane and a flow pathway for moving fluid across cells growing on the membrane to apply shear stress on the cells. Another embodiment of the device includes a body having flow shafts into which slides are placed. Fluid flows through the flow shafts over the slides to apply shear stress to cells growing on the slides.

17 Claims, 23 Drawing Sheets

OTHER PUBLICATIONS

Brunette, "Mechanical Stretching Increases the Number of Epithelial Cells Synthesizing DNA in Culture", J. Cell Sci. 69, 35–45 (1984).

Somjen et al., "Bone Remodelling Induced by Physical Stress is Prostaglandin $E_2$ Mediated", Biochimica et Biophysica Acta, 627 (1980) 91–100.

Banes et al., A New Vacuum–Operated Stress–Providing Instrument That Applies Static or Variable Duration Cyclic Tension or Compression to Cells In Vitro, J. Cell Sci. 75 (1985) pp. 1–8.

Leung et al., "A New In Vitro System for Studying Cell Response to Mechanical Stimulation", Exp. Cell Res. 109 (1977), pp. 285–298.

Winston et al., "The In Vitro Response of Endothelium to Mechanical Loading", $38^{th}$ ACEMB (1985), p. 88.

Winston et al., "Response of Endothelial Cells in Culture to Biaxial Deformation", Northeast Bioengineering Conference, University of Pittsburgh, (1987), 2 pp.

Thibault et al., "Mechanical Characterization of Membrane-like Biological Tissue", J. Biomechanical Engr., (1982), pp. 1–8.

* cited by examiner

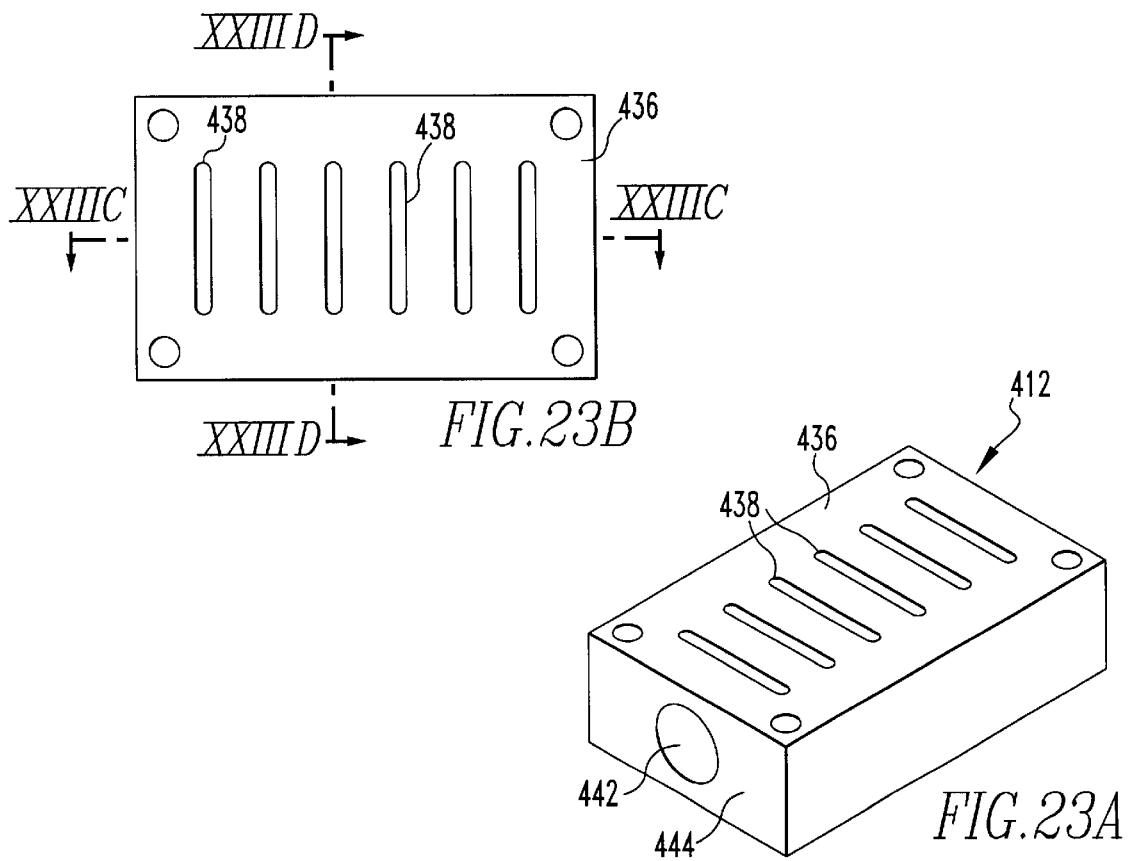
FIG.23B
FIG.23A
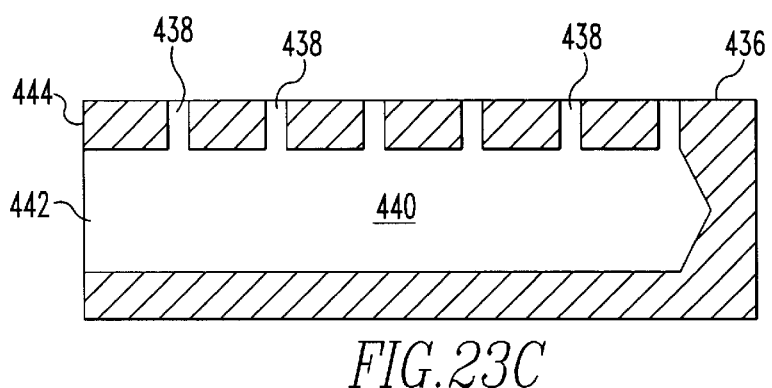
FIG.23C
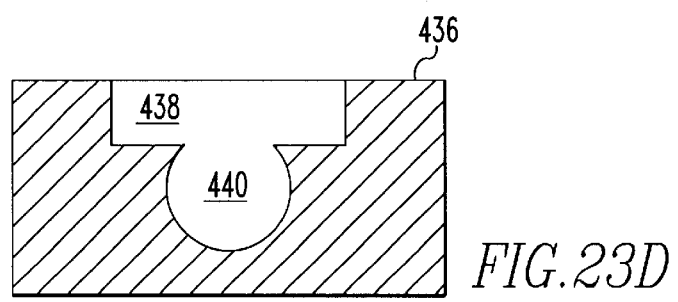
FIG.23D

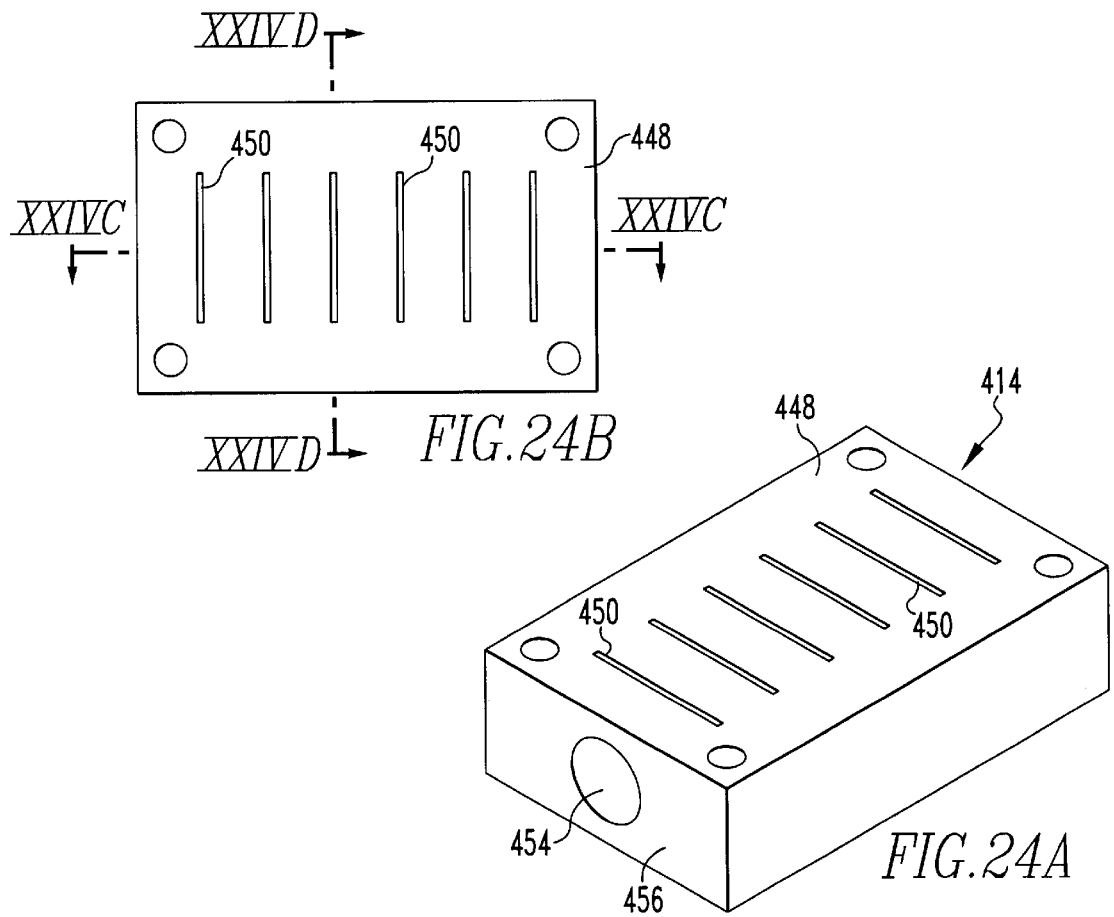
FIG.24B
FIG.24A
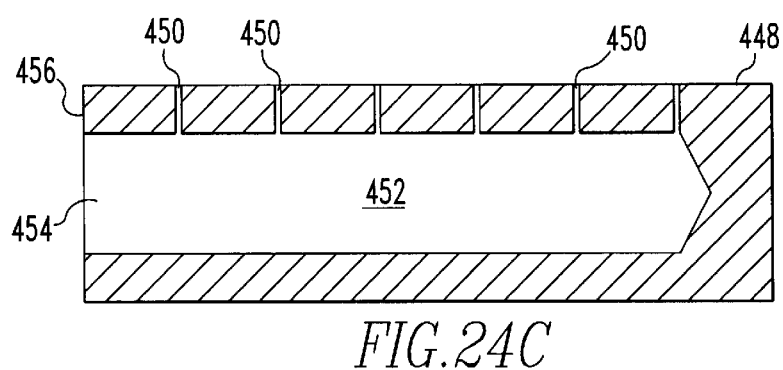
FIG.24C
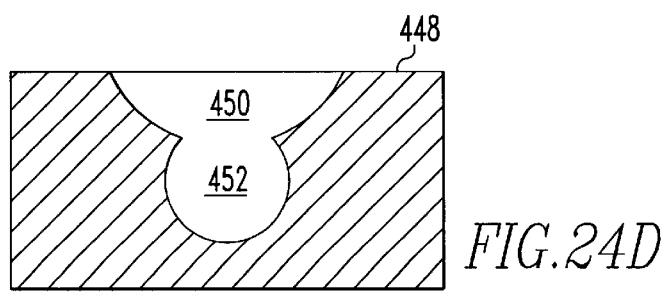
FIG.24D

APPARATUS FOR GROWING CELLS IN CULTURE UNDER SHEAR STRESS AND/OR STRAIN

RELATED APPLICATION

This application is a continuation-in-part of U.S. patent application Ser. No. 09/454,327, filed Dec. 3, 1999, entitled "Apparatus for Growing Cells in Culture Under Shear Stress and/or Strain" which claims the benefit of U.S. Provisional Patent Application Ser. No. 60/111,023, filed Dec. 4, 1998, entitled "Apparatus for Growing Cells in Culture Under Shear Stress and/or Strain".

BACKGROUND OF THE INVENTION

1. Field of the Invention

The present invention is directed toward a cell culture assembly used in the biomedical science field of tissue engineering and, more specifically, to a cell culture assembly through which fluid may flow for applying deformations to cells that include fluid-induced stress or substrate-induced strain to cultured cells.

2. Prior Art

In the human body, many cells are constantly subjected to stress from fluid flow. Fluid flow in the body includes blood flow through the vasculature, lymph in the lymphatics, cerebrospinal fluid flow, any secretion in ducts, and also the movement of interstitial fluid in the matrix between and among cells in any tissue. Stressing cells in culture simulates the in vivo environment, causing dramatic morphologic changes and biomechanical responses in the cells. There are both long and short-term changes that occur when cells are stressed in culture, such as alterations in the rate and amount of protein expression and secretion, the rate of cell division and alignment, changes in energy metabolism, changes in rates of macromolecular synthesis or degradation, and other changes in biochemistry and bioenergetics. Prior devices have been developed for applying substrate deformation on cells and applying fluid-induced shear stress by subjecting the cells to fluid flow. However, none of these devices have allowed for alternating or simultaneous application of both types of mechanical loading of cells in vitro and for quantitation of the applied stresses and strains.

A need remains for a cell culture assembly in which cells may be cultured and subjected to fluid-induced shear stress which is precisely controlled.

SUMMARY OF THE INVENTION

Accordingly, I have developed a cell culture assembly including a body having a flow surface extending across an upper surface of the body. The top surface of the body may also be used as a flow surface on which cells may be cultured. Moreover, a flexible membrane may be clamped by the body and also be used as a flow surface on which cells may be cultured. This rubber membrane may also be deformed by vacuum so this cell receives substrate tension in unconstrained distension may be deformed by stretching across a planar faced post so that the flexible substrate is deformed equibiaxially. Positive pressure may also be applied to deform the flexible membrane upward to apply a compressive deformation to overlying cells cultured on the top member. Both fluid stress and substrate strain may also be delivered simultaneously as often occurs in blood vessels or in other tissues.

The body further defines a passageway in fluid communication with the flow surface and a cover member covering the flow surface. The flow surface of the body and the cover member thereby define a flow chamber through which fluid may flow. A cell culture surface is positioned on the flow surface or on the cover or both. Cells cultured on the cell culture surface are subject to shear stress when fluid flows through the passageway and the flow chamber.

In one embodiment of the invention, the body has an upper surface defining a first opening therethrough. The assembly further includes a base attached to the body and a cell culture membrane fixed between the base and the body whereby the membrane covers the first opening, such that when fluid flows through the body passageway, the fluid passes across the membrane thereby inducing shear stress on cells growing on the membrane. The body passageway includes a pair of bores defined in the body on opposing sides of the first opening, wherein each bore extends between a side of the body and the upper surface. The upper surface defines a pair of second openings, preferably in the form of slits, on opposing sides of the first opening and each second opening is in fluid communication with one of the bores. A gasket is positioned on the body upper surface and surrounds the first opening and the second openings. The gasket is configured to retain fluid flowing out of one of the second openings and into the other second opening. A port is defined in the body for connection to a pressure supply. The body upper surface further defines an annular channel in fluid communication with the port. The gasket overlies the channel and the cover overlies the gasket. The gasket defines a plurality of holes which overlie the annular channel such that the cover seats on the gasket when negative pressure is applied to the port. Alternatively, the upper surface may be clamped by overlying pressure to the gasket and body by conventional assemblies such as a plate and fasteners.

The base comprises an annular member defining a chamber and having a wall with a top surface on which the membrane is seated. An insert is received within the chamber. The insert includes a support member with a support surface for supporting a portion of the membrane. The wall of the base defines an aperture and the insert defines an insert passageway extending between a side of the insert and the insert support surface where the insert passageway is in fluid communication with the aperture of the base wall. When negative pressure is applied to the chamber through the aperture, the membrane is urged against the insert support surface. Preferably, the insert includes a post spaced apart from the support member thereby defining an annular gap between the post and the support member. An opening defined in the support member is in fluid communication with the gap. Preferably, an upper surface of the post is lower than the support surface and an upper surface of the portion of the membrane supported by the support surface is in a plane of the upper surface of the body.

In another embodiment of the invention, the body includes a flow member and a pair of end members attached to opposing ends of the flow member, where the opposing ends of the flow member each define a recess, and where each flow surface extends between the recesses in the ends of the flow member. In this arrangement, the openings are defined in the end members and are in fluid communication with the recesses. An annular channel is defined in an upper surface of the body and surrounds the flow surface. The body defines a port in fluid communication with the channel whereby when negative pressure is applied to the port, the cover is urged toward the body. A gasket defining an opening aligned with the flow surface and defining a plurality of holes therethrough is positioned between the body and the cover. The gasket opening overlies the flow surface and the holes overlie the channel, such that when negative pressure is applied to the port, the cover sealingly seats on the gasket and the gasket sealingly seats on the body. The flow chamber is defined by the gasket, the cover and the recess. The body may include a plurality of flow surfaces with the channel surrounding each flow surface defined in the body, and the gasket defining a plurality of openings each overlying a flow surface. Each end of the body then defines a plurality of openings aligned with each of the flow surfaces.

Another embodiment of the invention includes a body, a top, and a bottom in fluid communication with each other for the steady flow of fluid therethrough. The body has a plurality of flow shafts extending therethrough. The flow shafts are preferably substantially parallel to each other. A plurality of slides is inserted into the plurality of flow shafts. Cells are cultured on the plurality of slides. The top is in fluid communication with the plurality of flow shafts. The bottom is also in fluid communication with the plurality of flow shafts. Fluid is delivered, via the top and/or the bottom, to the flow shafts to simulate the stresses on the cells in blood vessels or other tissues caused by fluid flow.

The body of the assembly may include O-ring grooves surrounding each end of the plurality of flow shafts. O-rings are placed in the O-ring grooves to ensure a leakproof seal between the body and the top and bottom when assembled. Alternatively, O-ring grooves may be located on the top or bottom to surround each end of the plurality of flow shafts when the assembly is assembled.

DESCRIPTION OF THE DRAWINGS

A complete understanding of the invention will be obtained from the following description when taken in connection with the accompanying drawing figures wherein like reference characters identify like parts throughout.

FIG. 23A is a perspective view of the top member shown in FIG. 21;

FIG. 23B is a top view of the top member shown in FIG. 21;

FIG. 23C is a cross-sectional front view taken along line XXIIIC—XXIIIC of the top member shown in FIG. 23B;

FIG. 23D is a cross-sectional side view taken along line XXIIID—XXIIID of the top member shown in FIG. 23B;

FIG. 24A is a perspective view of the bottom member shown in FIG. 21;

FIG. 24B is a top view of the bottom member shown in FIG. 21;

FIG. 24C is a cross-sectional front view taken along line XXIVC—XXIVC of the bottom member shown in FIG. 24B;

FIG. 24D is a cross-sectional side view taken along line XXIVD—XXIVD of the bottom member shown in FIG. 24B;

DETAILED DESCRIPTION OF THE PREFERRED EMBODIMENTS

Figure 1:
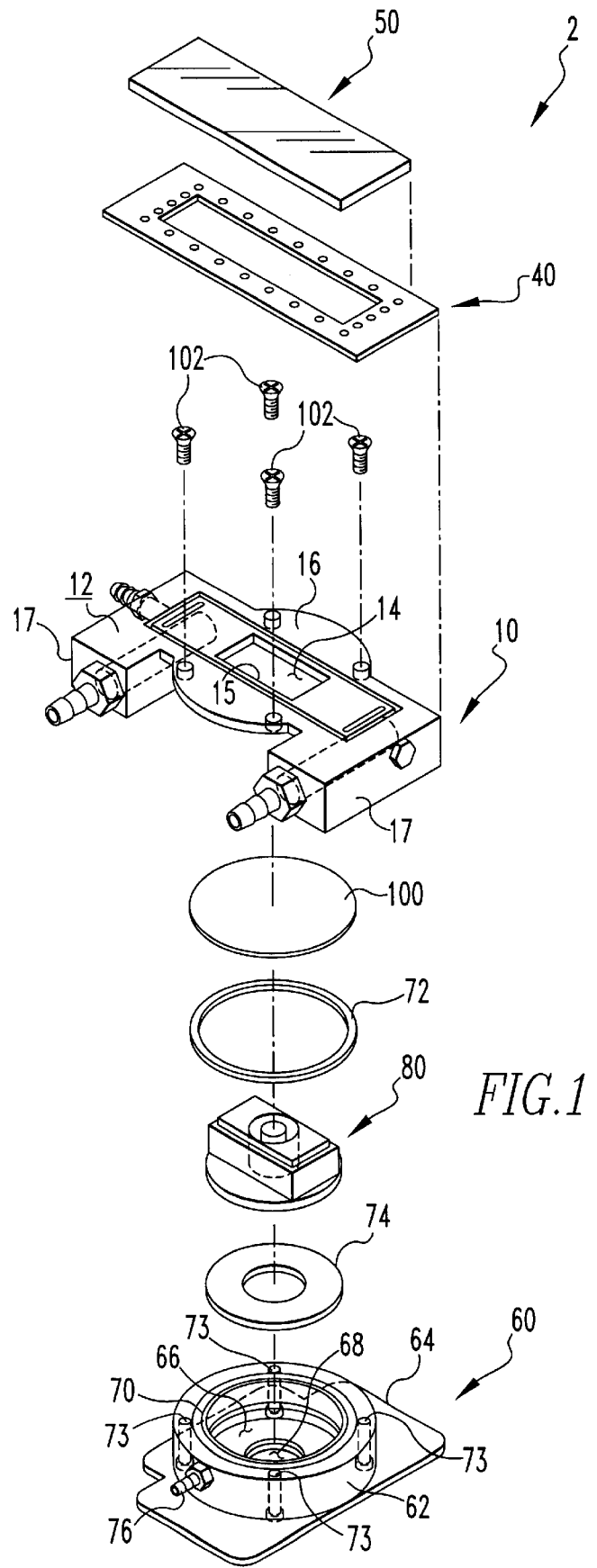
FIG. 1 is an exploded perspective view of a cell culture assembly made in accordance with the present invention including a body, an insert and a base.

For purposes of the description hereinafter, the terms "upper", "lower", "right", "left", "vertical", "horizontal", "top", "bottom" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting. A complete understanding of the invention will be obtained from the following description when taken in connection with the accompanying drawing figures wherein like reference characters identify like parts throughout.

The present invention includes a cell culture assembly for applying shear stress to cells. One embodiment of the invention is the cell culture assembly 2 shown in FIGS. 1 and 2 which includes a body 10 through which fluid may flow. The body 10 shown in detail in FIGS. 2–5 includes an upper surface 12 which defines a central opening 14 surrounding a rim 15 centrally located in a central planar portion 16 of the upper surface 12. The opening 14 and rim 15 are preferably rectangular in shape. The planar portion 16 is disposed between a pair of integrally formed housings 17. Preferably, the body 10 is formed from aluminum, but stainless steel, lucite or other like materials may be used in the fabrication.

Figure 4:
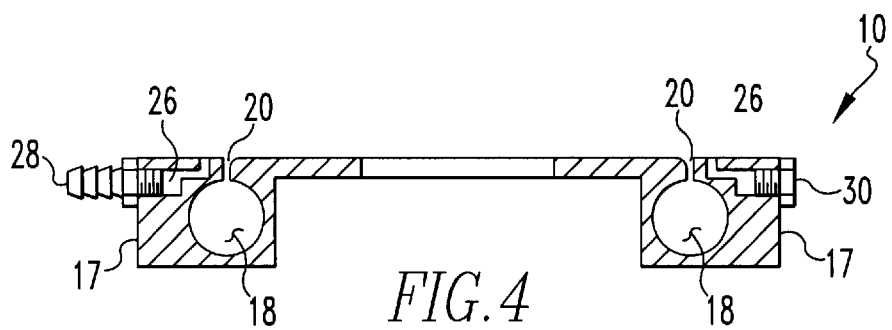
FIG. 4 is a partial sectional view of the body taken along lines IV—IV in FIG. 3.
Figure 5:
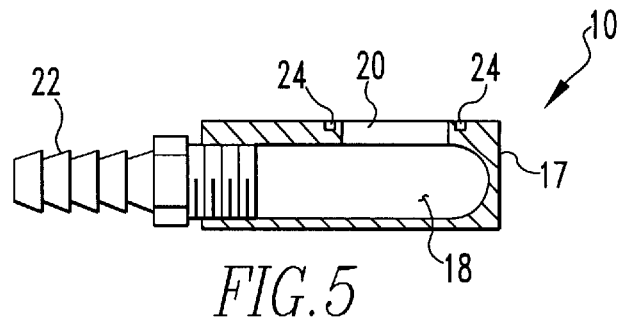
FIG. 5 is a partial sectional view of the body taken along lines V—V in FIG. 3.

Referring to FIGS. 4 and 5, a bore 18 is defined in each of the housings 17 on opposing ends of the body 10. Each bore 18 is in fluid communication with a slit 20 defined in the upper surface 12. The bores 18 are each preferably internally threaded to accept a fitting 22. The fittings 22 may constitute quick disconnect valves instead of the particular fitting shown in FIGS. 3 and 5. Also defined in the upper surface 12 is a continuous channel 24, preferably having a rectangular configuration. The channel 24 surrounds the central opening 14 and the slits 20. The shorter sides of the rectangular channel 24 are each in fluid communication with a vacuum opening 26 defined in each of the ends of the body 10. The vacuum openings 26 in the ends of the body are preferably internally threaded to accept a vacuum fitting 28 at one end and a sealing nut 30 at the other end. Either end of the body 10 may accept either of the vacuum fitting 28 or the nut 30.

Figure 2:
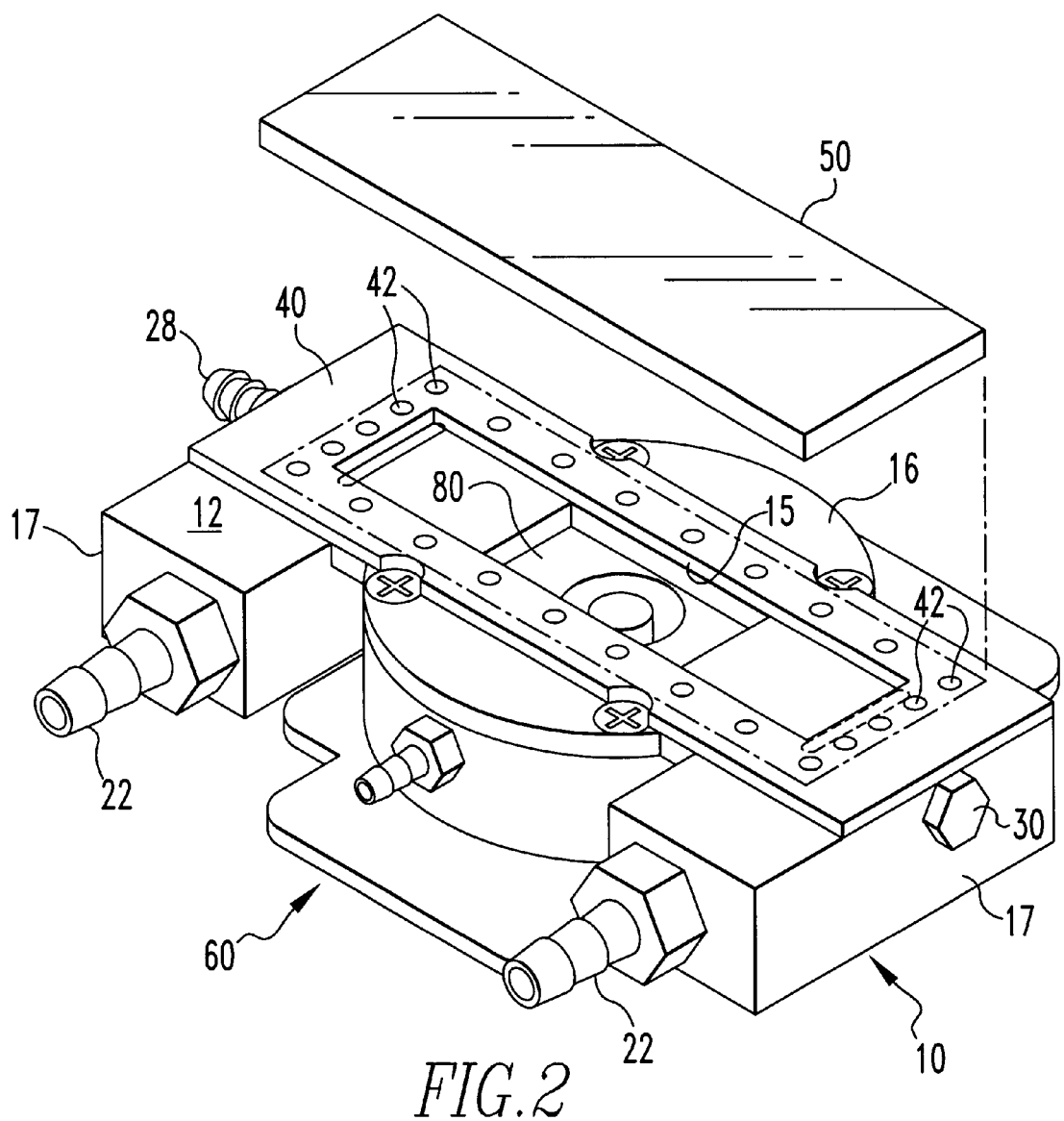
FIG. 2 illustrates a perspective view of the cell culture assembly depicted in FIG. 1, partially assembled.
Figure 3:
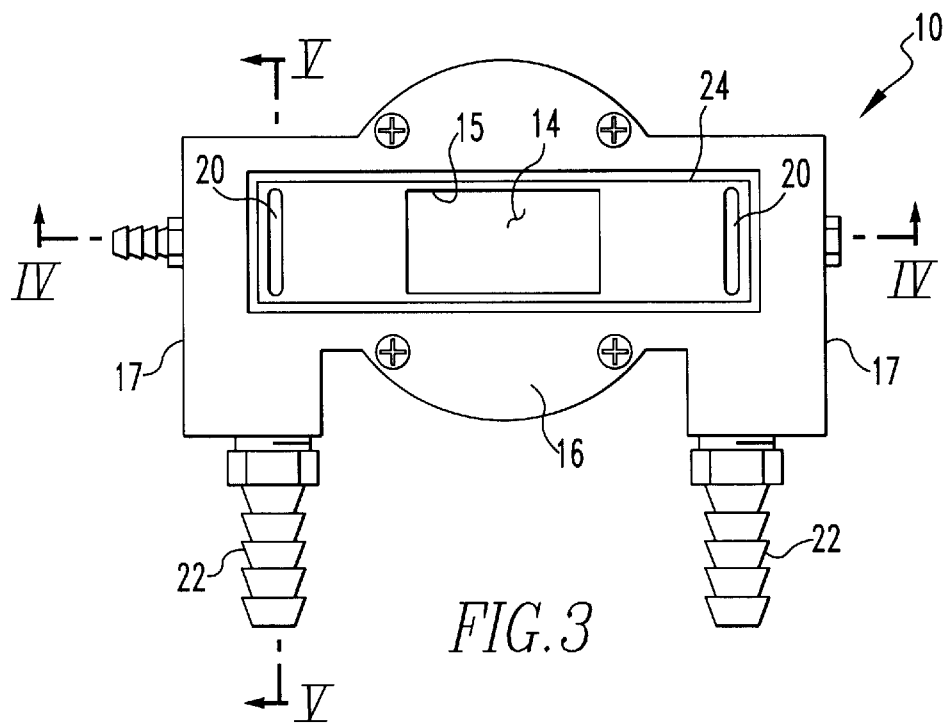
FIG. 3 is a plan view of the body shown in FIG. 1.

Referring to FIGS. 1 and 2, overlying the body 10 is a gasket 40, preferably having a configuration which coordinates with the configuration of the channel 24. The gasket 40 shown in FIGS. 1 and 2 is rectangular in shape so that the gasket 40 covers the channel 24 while leaving exposed the slits 20 and the central opening 14. The gasket 40 is preferably formed from a silicone rubber and includes a two-sided acrylic-silicone mastic (not shown) adhered to one side. The silicone side of the mastic is adhered to the gasket 40 and the acrylic side is adhered to the upper surface 12 of the body 10. A plurality of apertures 42 is defined in the gasket 40 at locations whereby the apertures 42 are in overlying relation to the channel 24 defined in the upper surface 12 of the body 10. The gasket 40 is shown in FIG. 2 as covering a portion of the upper surface 12. However, the gasket may completely cover the entire upper surface 12 to enhance the seal formed thereby. A cover 50 such as a glass microscope slide is positioned over the gasket 40. Upon application of a vacuum through one of the vacuum openings 26 in an end of the body 10 via the vacuum fitting 28, air is drawn through the apertures 42 in the gasket 40, through the channel 24 in the upper surface 12 and out through the vacuum opening 26 in the side of the body 10 and through the vacuum fitting 28. This causes the cover 50 to be pulled down in sealing engagement with the gasket 40.

Alternatively, the cover 50 may be clamped to the gasket 40 and body 10. Conventional clamping assemblies may be used to clamp the cover 50 to the gasket 40 and the body 10.

The cell culture assembly 2 further includes a base 60 as disclosed in co-pending U.S. application Ser. No. 09/201,570, entitled "Culture Plate for Applying Mechanical Load to Cell Cultures," incorporated herein by reference. The body 60 has a wall 62, preferably cylindrical in configuration, extending from a planar member 64 and defining a cylindrical well 66. The planar member 64 defines a base opening 68 having a diameter which preferably is smaller than an inner diameter of the well 66. The planar member 64 preferably is sized and configured for placement on the objective of a microscope. A groove 70 is defined in a top surface of the wall 62 and is sized to accept an O-ring 72. The top surface of the wall 62 also defines a plurality of threaded holes 73 used in assembling the assembly 2 as described below. A spacer 74 preferably formed from silicone in a ring shape is positioned within the well 66 on the planar member 64. A pressure differential supply fitting 76 extends outwardly from the wall 62 and communicates with the well 66 via an opening through the wall 62. An insert 80 (described in detail below) is received within the well 66 and seats on the spacer 74.

A flexible cell culture membrane 100 is disposed between the body 10 and the base 60. The body 10 clamps the membrane 100 and the O-ring 72 against the top surface of the wall 62 using conventional means such as a plurality of screws 102 threaded through a perimeter of the body planar portion 16 and into the threaded holes 73 in the base 60. A portion of the membrane 100 is exposed through the central opening 14. Cells are culturable on the exposed portion of the membrane 100. Alternatively, cells may be cultured on the cover 50. The integrity of a seal formed between the body 10, the membrane 100 and the base 60, thereby forming a flow chamber, is in part achieved by use of the insert 80 as described below.

Figure 6:
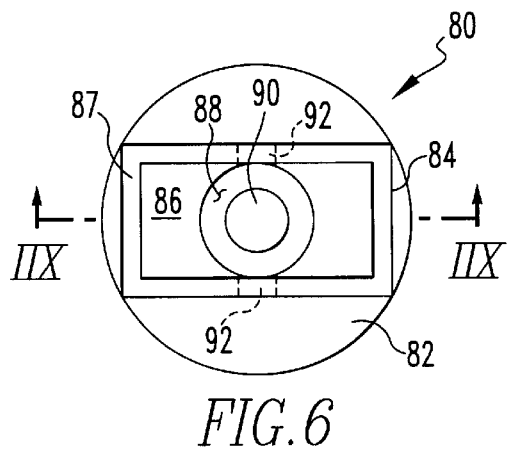
FIG. 6 is a plan view of the insert shown in FIG. 1.
Figure 8:
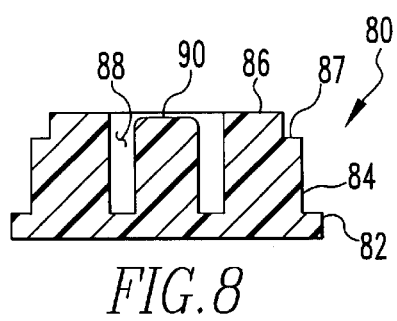
FIG. 8 is a cross-sectional view of the insert taken along lines VIII—VIII shown in FIG. 6.
Figure 7:
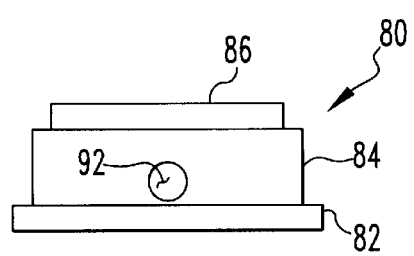
FIG. 7 is a side view of the insert shown in FIG. 6.

The insert 80 shown in FIG. 1 is shown in detail in FIGS. 6–8. The insert 80 includes a planar member 82 and a support member 84 bearing a support surface 86 extending therefrom. The support member 84 includes a ledge 87. The ledge 87 is sized to accept and mate with the rim 15 of the planar portion 16 surrounding the central opening 14. In this manner, the membrane 100 is clamped between the rim 15 of the body 10 and the ledge 87 of the insert 80. The support member 84 defines an annular opening 88 surrounding a post 90. As may be seen in FIG. 8, an upper surface of the post 90 is lower than the support surface 86. A layer of lubricating material (not shown), such as silicone, may be positioned on the top of the post 90 such that the support surface 86 and surface of the lubricating material are in a common plane. A passageway 92 is defined in each of two opposing sides of the support member 84 with each passageway 92 being in fluid communication with the annular opening 88. The post 90 may be one of a variety of geometrical shapes such as conical or frustoconical or have a constant rectangular or square cross-sectional configuration.

In operation, when a pressure differential, e.g., negative pressure, is applied to the pressure differential supply fitting 76, air is drawn from the annular opening 88 through the passageways 92 and out the pressure differential supply fitting 76 so that the membrane 100 is urged downwardly over or upwardly above the support surface 86 and over the lubricating material covering the post 90. Negative pressure is also applied to the vacuum fitting 28 on the body 10 to pull the cover 50 against the gasket 40 seated on the body 10. Upon application of negative pressure to the base 60 and the body 10, fluid at a selected flow rate is directed into one of the fittings 22, through the corresponding bore 18, up through the corresponding slit 20, across the membrane 100 covering the central opening 14 and out through the opposing slit 20, the other bore 18 and the other fitting 22. The membrane 100 preferably extends through the central opening 14 in the body 10 so that the fluid flows smoothly across one portion of the upper surface 12 on one side of the central opening 14, over cells growing on the membrane 100 and across the other portion of the upper surface 12. In this manner, the amount of flow to induce stress on cells growing on the membrane 100 from fluid flow thereover may be altered and studied. The flow rate of fluid passing through the body 10 can be controlled and the shear stress on cells growing on the membrane 100 may be calculated. By varying the flow rate to the body 10, varying degrees of shear stress may be applied to cells. Hence, the impact of shear stress on the cells can be determined quantitatively. The membrane 100 preferably is formed from a transparent material so that the entire assembly may be placed on a microscope. The effect of fluid flow and stress therefrom on cells growing on the membrane 100 may be actively studied.

Although not shown in the drawings, the assembly 2 preferably includes a fluid pump, preferably a peristaltic pump, one or more fluid pulse dampeners, a digital flow meter, valves to regulate fluid sampling of flow to the assembly 2 and a fluid reservoir. All components are connected with flexible tubing in a continuous or discontinuous flow loop. The fluid flowing through the assembly 2 may be recycled therethrough in a continuous loop. In this manner, substances secreted by the cultured cells interact with the cells. Alternatively, the fluid may not be returned to the assembly 2 so that secreted substances do not effect the cells. The assembly 2 may further include a sampling port into the fluid effluent leaving the body 10. Fluid withdrawn can be biochemically analyzed.

Control of fluid flow is achieved by regulation of the pump flow rate, the bore size of the tubing and the opening and closing of a valve or valves positioned upstream of the flow chamber, downstream of the flow chamber or in both locations. Flow control may be achieved by regulation of the pump flow rate alone. The flow rate may range from picoliters to milliliters of total flow to continuous flow of fluid. Alternatively, the pump flow rate may be maintained at a constant rate and the valves may be opened and closed to direct fluid flow away from the flow chamber to provide rapid regulation of flow rate, particularly for rapid oscillations in the flow stream. Alternatively, the valves may be used to provide flow reversals to the flow chamber so that fluid enters the chamber from one direction at one instant then reverses direction and enters from the opposite side of the chamber at the next instant. These levels of flow control permits both continuous fluid flow, and discontinuous fluid flow, the latter as a pulsating flow or a flow reversal, as occurs in the vasculature, lymphatics and in interstitial fluid flow in tissues. The precise nature of the rate of fluid flow, and type of fluid flow may have unique consequences for the response(s) of the cells or tissue experiencing the deformation. This is particularly true when fluid flow is combined with substrate strain. This is an imperative point for cells that may be "conditioned" by this mechanical environment and transferred to a location in the body in a tissue engineering application where they must withstand the rigors of the mechanically active environment of the body.

Figure 9:
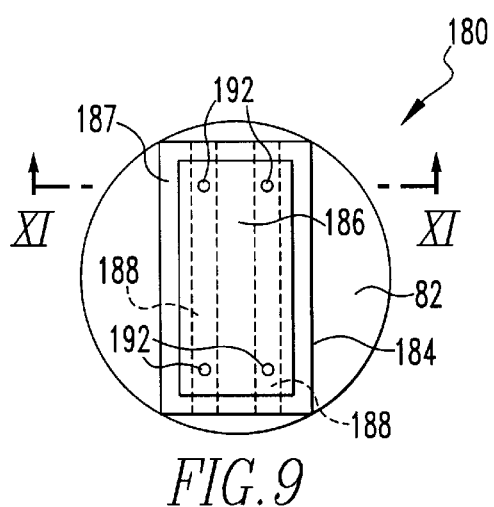
FIG. 9 is a plan view of an alternative insert made in accordance with the present invention.
Figure 11:
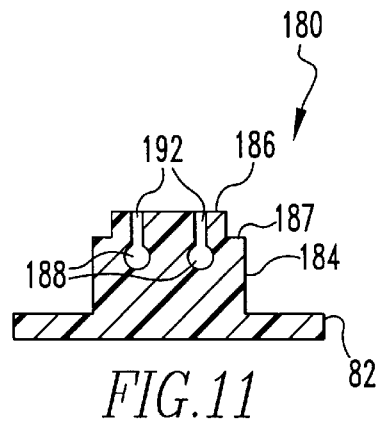
FIG. 11 is a cross-sectional view of the insert taken along lines XI—XI in FIG. 9.
Figure 10:
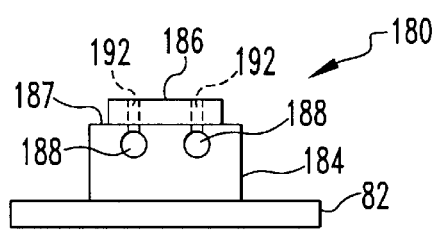
FIG. 10 is an end view of the insert shown in FIG. 9.

FIGS. 9–11 show an alternative insert 180. The insert 180 includes a support member 184 extending from a planar member 82 and including a substantially planar support surface 186 and a ledge 187. The support surface 186 is preferably rectangular in configuration. A plurality of, preferably two, bores 188 extends longitudinally through the support member 184. A plurality of, preferably four, holes 192 is defined in the support surface 186 and communicates with the bores 188. When insert 180 is used instead of the insert 80 in the assembly 2, the membrane 100 is clamped between the rim 15 of the body 10 and the ledge 187 of the insert 180 thereby maintaining the membrane 100 flat across the support surface 186. Negative pressure applied to the fitting 76 pulls air through the holes 192 and out through the bores 188, the well 66 and the fitting 76. The insert 180 serves to ensure uniformity in the flatness of the membrane 100.

Figure 12:
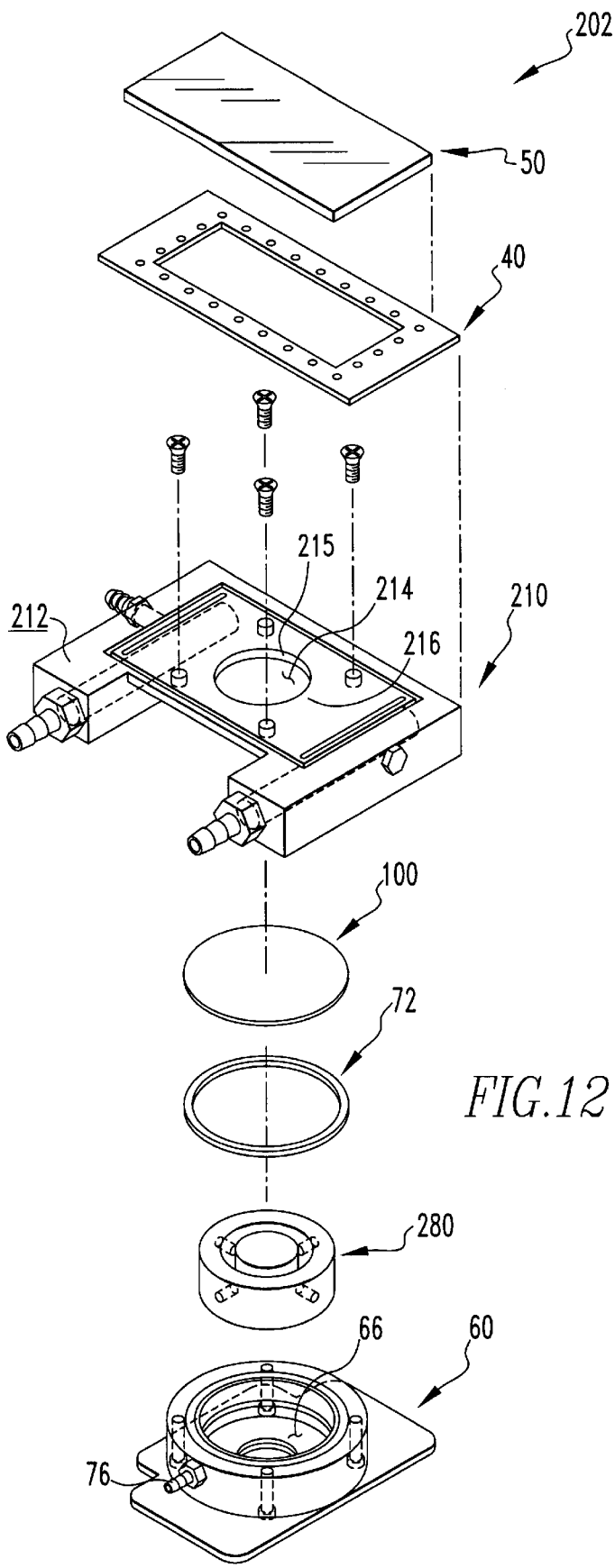
FIG. 12 is an exploded perspective view of another embodiment of a cell culture assembly made in accordance with the present invention including an insert.

Another embodiment of the invention is the cell culture assembly 202 shown in FIG. 12. The cell culture assembly 202 includes a cover 50, a gasket 40, a membrane 100, an O-ring 72 and a base 60 similar to those components described above in connection with assembly 2. However, assembly 202 includes a body 210 having an upper surface 212 which defines a central opening 214 surrounding a rim 215 which is preferably circular in configuration and centrally located in a central portion 216. All other components of the body 210 are similar to those of the body 10.

Figure 13:
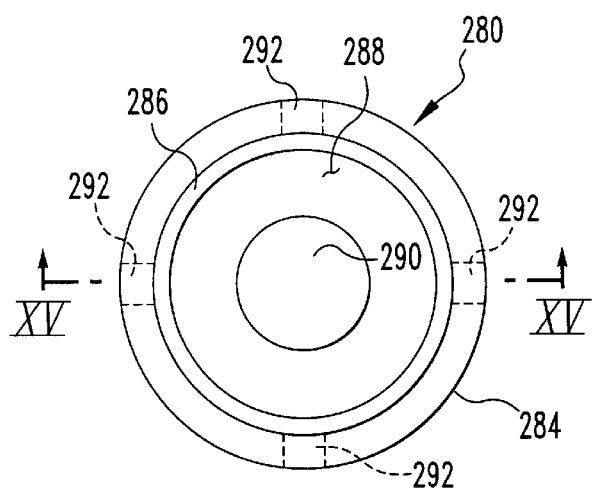
FIG. 13 is a plan view of the insert shown in FIG. 12.
Figure 14:
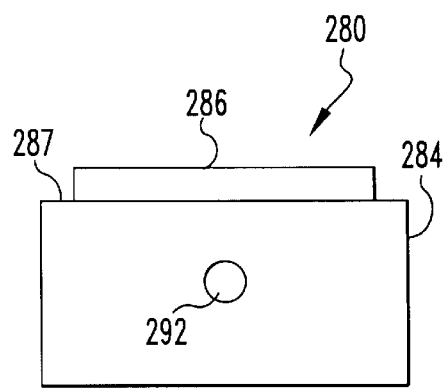
FIG. 14 is a side view of the insert shown in FIG. 13.
Figure 15:
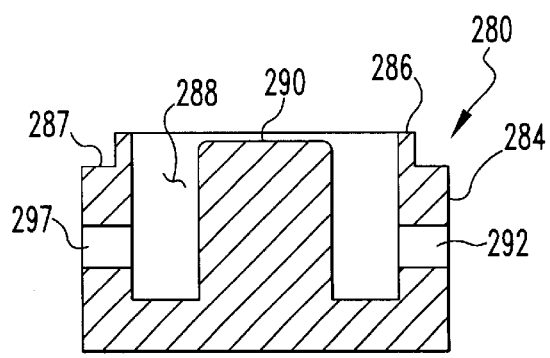
FIG. 15 is cross-sectional view of the insert taken along lines XV—XV in FIG. 13.

An insert 280 is received within the well 66. As shown in more detail in FIGS. 13–15, the insert 280 has a support member 284 with a preferably overall cylindrical shape. A ring-shaped support surface 286 stepped up from a ledge 287 supports the membrane 100 when the body 210 and the base 60 are clamped together with the membrane 100 therebetween. The ledge 287 is sized to accept and mate with the rim 215 of the body 210 surrounding the central opening 214. In this manner, the membrane 100 is clamped between the central portion 216 and the ledge 287. Cells may be cultured on the portion of the membrane 100 which is exposed through the central opening 214. The support member 284 defines an annular opening 288 surrounding a post 290. As can be best seen in FIG. 15, an upper surface of the post 290 is lower than the support surface 286. As is true for insert 80, a layer of lubricating material (not shown) may be placed on the top of the post 290 such that the support surface 286 and surface of the lubricating material are in a common plane. A plurality of, preferably four, holes 292 are defined in the support member 284 and communicate with the annular opening 288 and the well 66. When negative pressure is applied to the fitting 76, air is drawn from the annular opening 288 out through the holes 292, the well 66 and the fitting 76 to pull the membrane 100 against the support surface 186.

Yet another embodiment of the invention is shown in FIGS. 16–20. The cell culture assembly 302 shown in FIGS. 16 and 17 includes a preferably rectangular shaped body 310, a gasket 340 and a cover 350.

Figure 16:
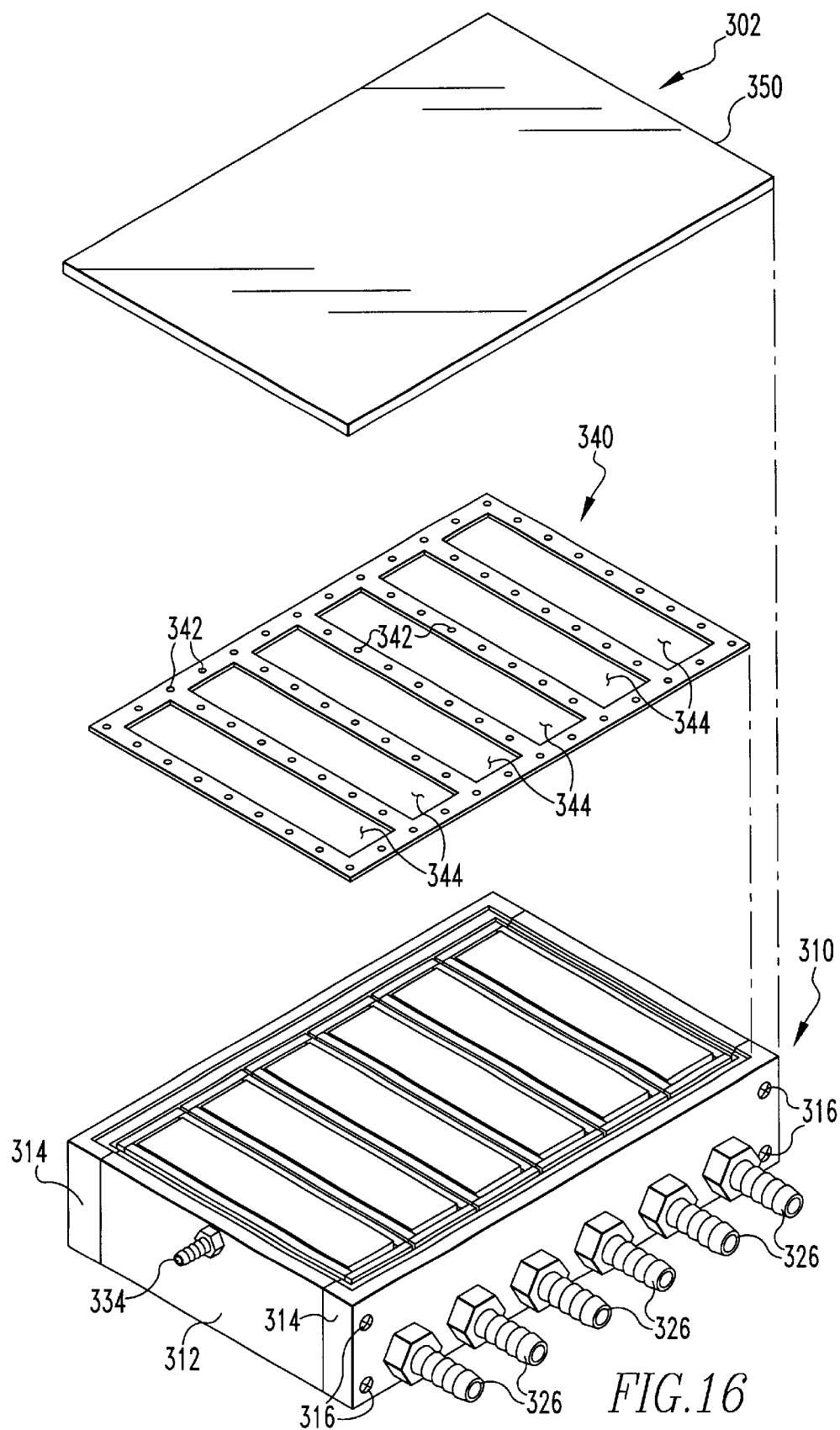
FIG. 16 is an exploded perspective view of another embodiment of the cell culture assembly made in accordance with the present invention including a cover, a gasket and a body.
Figure 17:
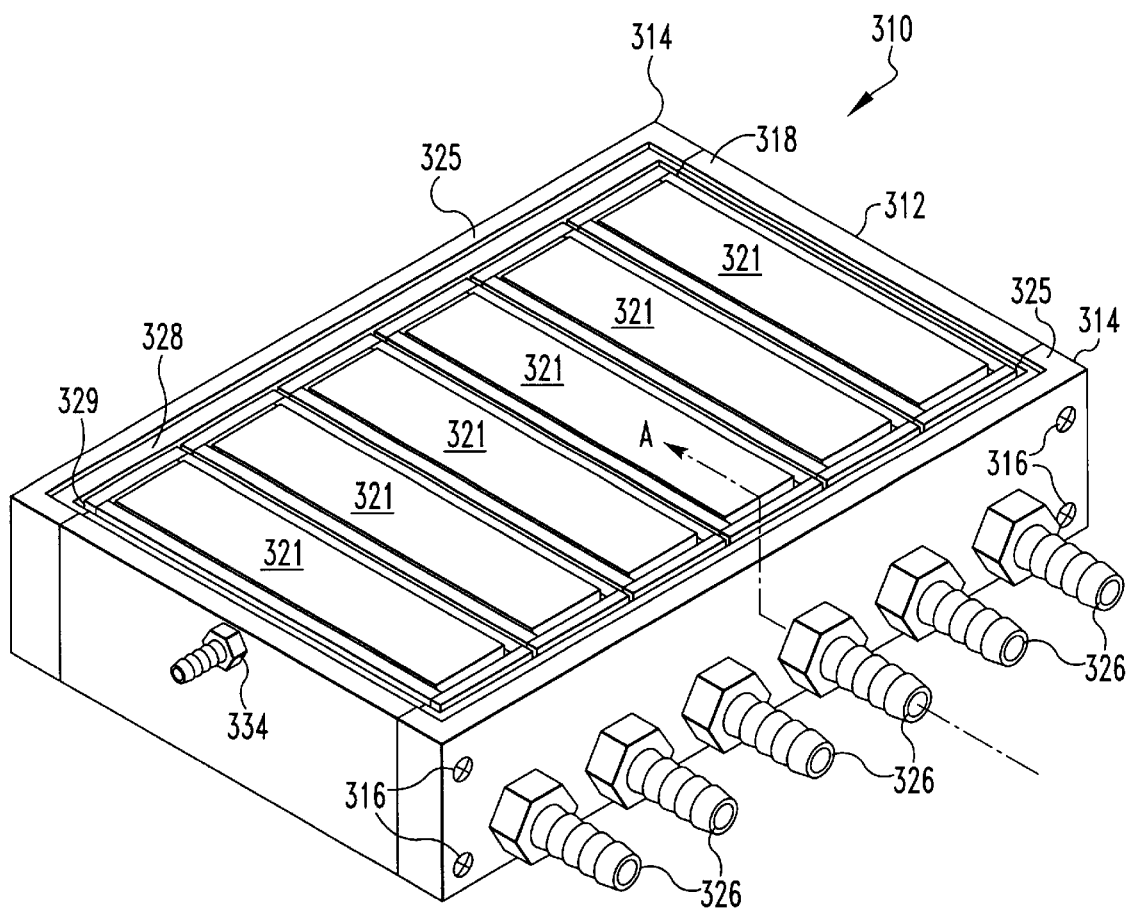
FIG. 17 is a perspective view of the body shown in FIG. 16.
Figure 18:
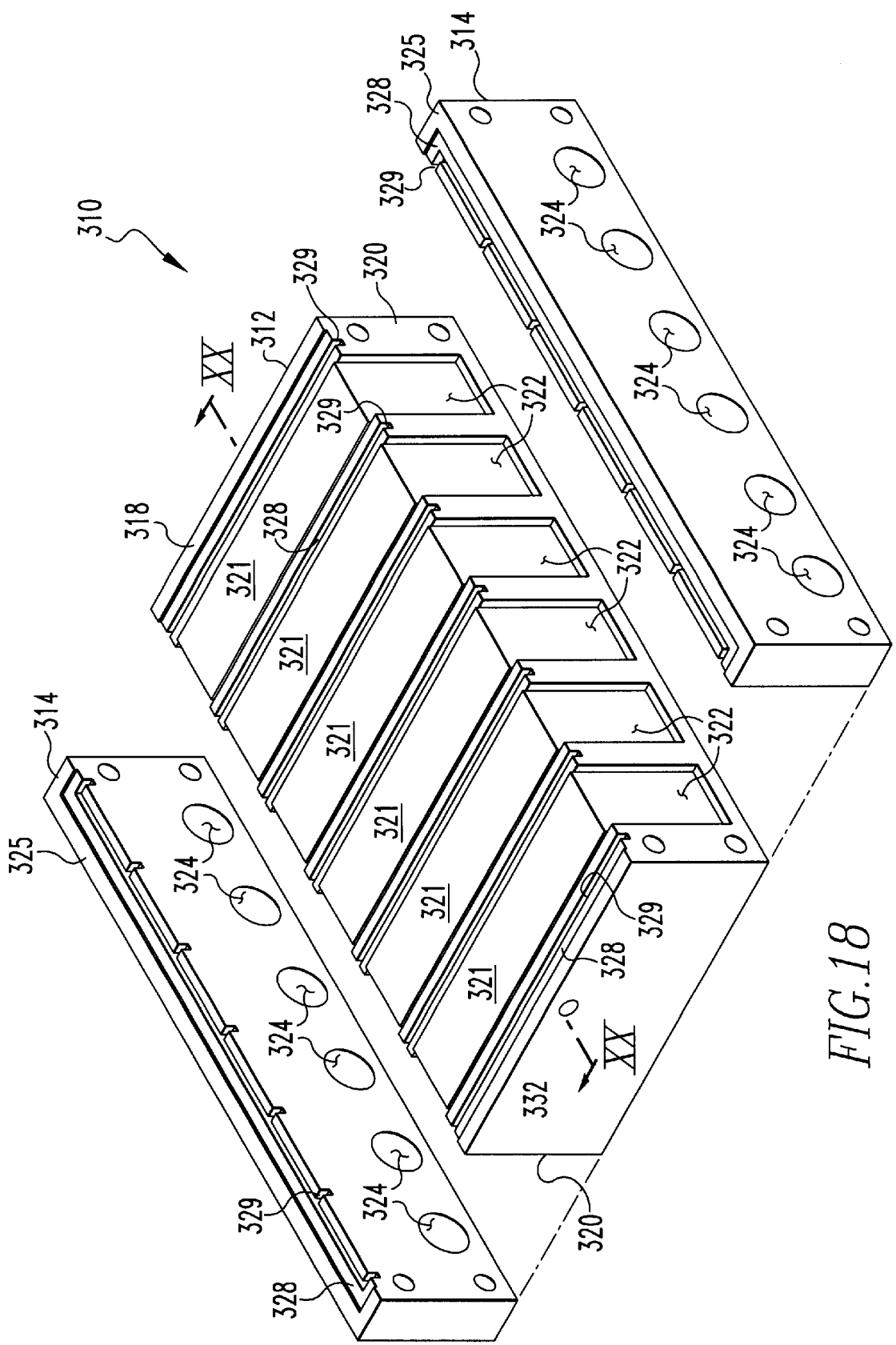
FIG. 18 is an exploded perspective view of the body shown in FIG. 17 including a flow member and end pieces.
Figure 19:
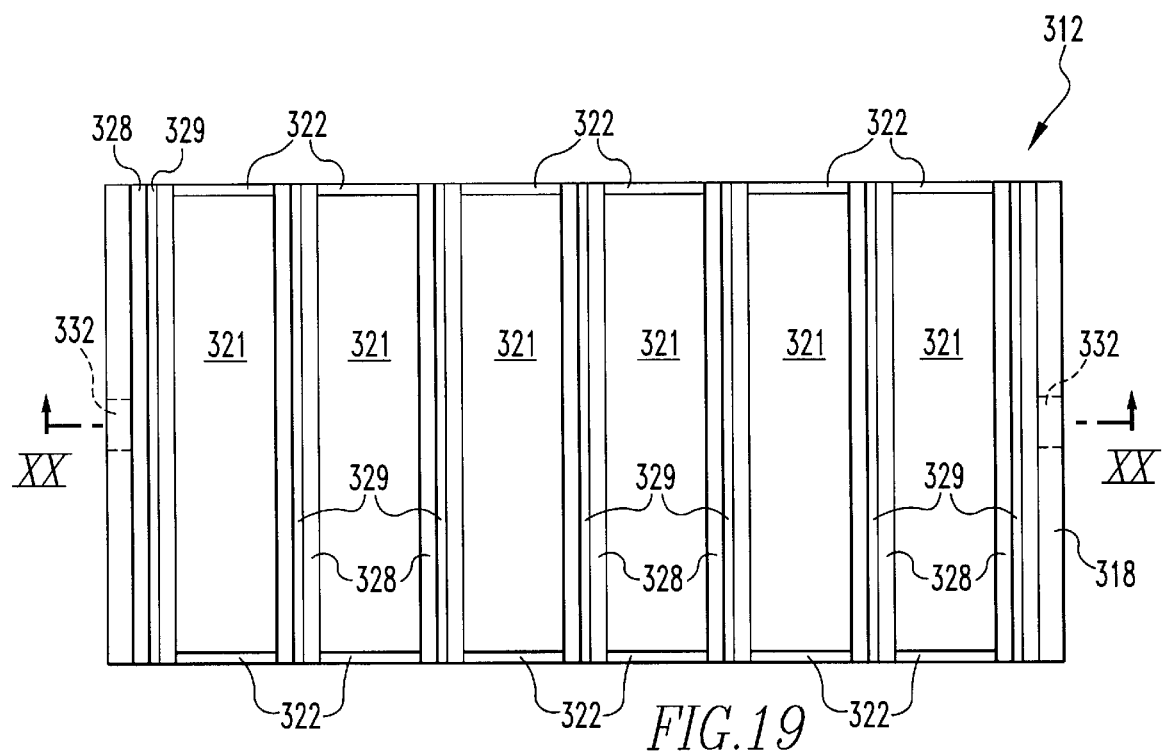
FIG. 19 is a plan view of the flow member shown in FIG. 18.

As shown in FIG. 18, the body 310 preferably includes a multi-sectional flow member 312 and a pair of end pieces 314. The end pieces 314 are fixed to the flow member 312 using screws 316 (FIGS. 16 and 17) or other conventional securing mechanisms. The flow member 312 includes a top surface 318 and a pair of opposing end surfaces 320 (only one being shown). The top surface 318 includes a plurality of flow surfaces 321. A plurality of recesses 322 corresponding in number to the number of flow surfaces 321 is defined in each of the end surfaces 320 and are in fluid communication with the flow surfaces 321. The end pieces 314 each define a plurality of openings 324 and have a top surface 325. Each opening 324 is aligned with one of the recesses 322 and is internally threaded to accept a fitting 326 (FIGS. 16 and 17). When the flow member 312 and the end pieces 314 are assembled as shown in FIG. 17, a plurality of pathways are formed for fluid to flow in the direction shown by arrow A via each set of fittings 326, openings 324, recesses 322 and flow surfaces 321 and out through the corresponding recesses 322, openings 324 and fittings (not shown) in the opposite end of the body 310.

Figure 20:
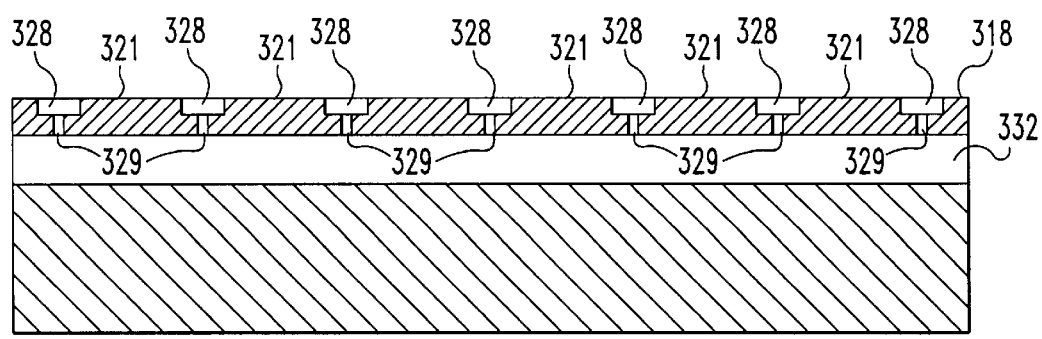
FIG. 20 is a cross-sectional view of the flow member taken along line XX—XX in FIG. 19.

A network of channels 328 having flow slits 329 is defined in the top surface of the body 310. The network of channels 328 is continuous when the body 310 is fully assembled as shown in FIGS. 16 and 17. The flow member 312 has channels 328 which extend parallel to the flow surfaces 321 along the length of the flow member 312. The end pieces 314 each have parallel channels 328 which mate with the channels 328 in the flow member 312 and a channel 328 perpendicular thereto which connects together each of the parallel channels 328. As best shown in FIGS. 18 and 20, an opening 332 is defined in the flow member 312 and extends between opposing sides of the flow member 312. The opening 332 is in fluid communication with the channels 328. A vacuum fitting 334 (FIGS. 16 and 17) is received in one end of the opening 332 and a sealing nut (not shown) is received in the other end of the opening 332.

The gasket 340, similar in material construction to gasket 40 such as molded silicone rubber, is placed over the top surfaces 318 and 325 to cover the network of channels 328. The gasket 340 defines a plurality of apertures 342 at spaced apart locations. When the gasket 340 is seated on the body 310, the apertures 342 are in overlying relation to the flow slits 329 in the channels 328. The gasket 340 also defines a plurality of flow openings 344 corresponding in number to the number of flow surfaces 321 of the flow member 312. Each flow opening 344 overlies one of the flow surfaces 321 of the flow member 312. The cover 350, preferably made of glass or Mylar, is positioned over the gasket 340. When assembled together, each set of a flow surface 321, gasket flow opening 344 and the cover 350 forms a flow chamber in fluid communication at the ends thereof with recesses 322. The thickness of the gasket 340 may be selected to provide a desired volume of fluid flowable through each flow opening 344. The cover 350 may also be clamped to the body 310 using conventional external clamps. The cover 350 may be sized to completely cover the body 310 (as shown in FIG. 16) or be sized to cover only the gasket 340.

In operation, fluid is supplied to the fittings 326 and flows through openings 324 in one end piece 314 and into the recesses 322 on one end of the flow member 312, over the flow surfaces 321 thereby filling the flow openings 344, into the other recesses 322 on the opposite end of the flow member 312 and out through the openings 324 in the other end piece 314. Negative or positive pressure is applied to the vacuum fitting 334 which draws air through the apertures 342 and out through the opening 332 and vacuum fitting 334. The cover 350 is pulled onto the gasket 340 thereby sealing the flow chambers formed at each flow opening 344. Cells may be cultured directly on the flow surfaces 321 or on an underside of the cover 350. Alternatively, a cell culture membrane (not shown), preferably formed from silicone, may be adhered to the underside of the cover 350. The flow rate of fluid applied to each flow chamber may be varied. One or more of the flow chambers may be used at one time. The flow may be continuous in one direction, the flow may be pulsed or the flow may be occasionally or periodically reversed as described above with respect to the assembly 2. In this manner, a variety of stresses may be applied to cultures of cells grown side-by-side in the assembly 302.

An example of the relative dimensions of the components of the assembly 302 are as follows. When the flow member 312 is 6 inches wide and 3.15 inches long, the flow surfaces 321 are 0.65 inch wide. The channels 328 are 0.25 inch wide and the slits 329 are 0.05 inch wide. The recesses 322 extend 1.125 inch downwardly and have a depth of 0.06 inch. The opening 332 is centered 0.15 inch down from the top surface of the flow member 312.

Figure 21:
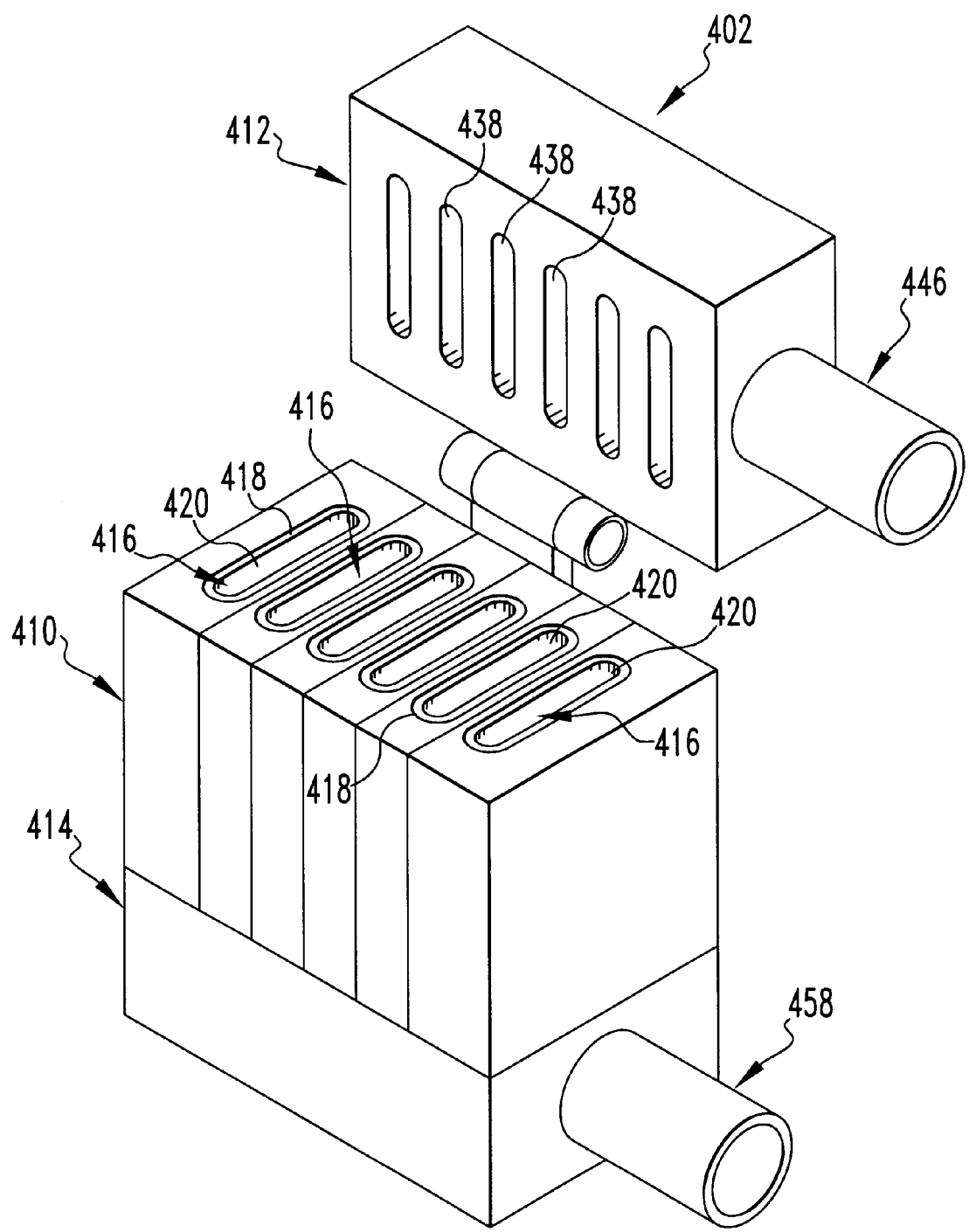
FIG. 21 is a perspective view of a multi-piece, straight flow cell culture assembly made in accordance with the present invention including a body, a top member, and a bottom member.
Figure 22A:
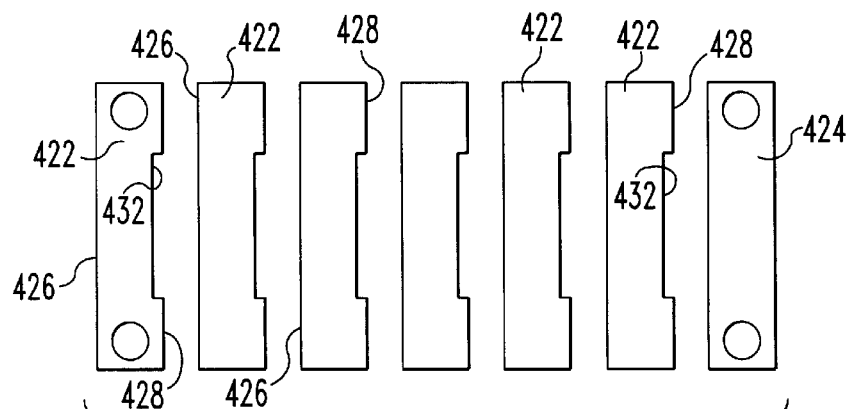
FIG. 22A is an exploded top view of the body shown in FIG. 21.
Figure 22B:
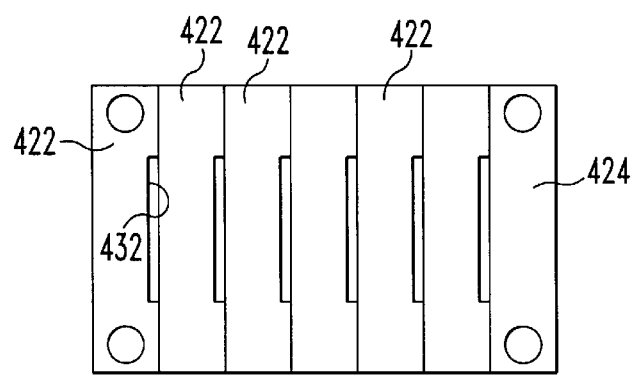
FIG. 22B is a top view of the body shown in FIG. 21.
Figure 22C:
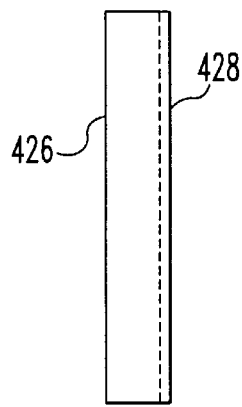
FIG. 22C is a side view of a body or end member of the body shown in FIG. 21.
Figure 25:
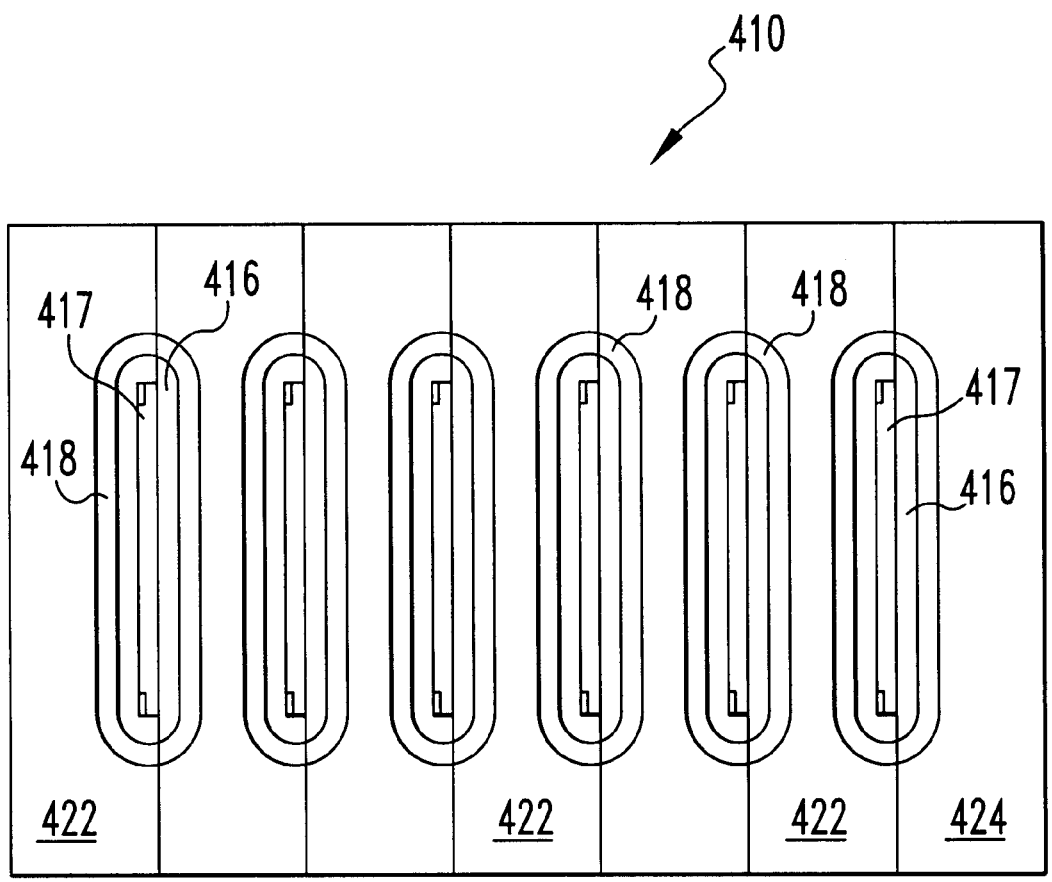
FIG. 25 is a top view of the body shown in FIG. 21 having O-ring slots.

Another embodiment of the invention is the cell culture assembly shown in FIG. 21 which includes a body, a top member, and a bottom member having passages defined therein for fluid communication with each other and the steady flow of fluid therethrough. The body has a plurality of flow shafts extending therethrough. The flow shafts are preferably substantially parallel to each other. A plurality of slides (FIG. 25) is inserted into the plurality of flow shafts. Cells are cultured on the plurality of slides. Flow slots in the top member are in fluid communication with the plurality of flow shafts in the body. Flow slots in the bottom member are also in fluid communication with the plurality of flow shafts in the body. Fluid is delivered, via the top member and/or the bottom member, to the flow shafts to simulate the stresses on the cells in blood vessels or other tissues caused by fluid flow.

The body 410 of the assembly 402 may include a plurality of O-ring grooves 418 surrounding each end of the plurality of flow shafts 416. O-rings (not shown) are placed in the O-ring grooves 418 to ensure a leakproof seal between the body 410 and the top member 412 and the bottom member 414 when assembled. Alternatively, O-ring grooves (not shown) may be located on the top member 412 or bottom member 414 to surround each end 420 of the plurality of flow shafts 416 when the assembly 402 is assembled.

One variation of this embodiment is a multi-section, straight flow cell culture assembly 402 as shown in FIGS. 22A–25. The body 410 includes a plurality of body sections 422 and an end section 424. The body and end sections 422, 424, respectively, are preferably generally rectangular in shape. The body sections 422 have a first surface 426 and a second surface 428. Each of the plurality of body sections 422 has a recess 432 on the second surface 428 which extends a length of the second surface 428. The plurality of body sections 422 is assembled in a parallel, side-by-side manner such that the second surface 428 with a recess 432 of one body section 422 aligns with the first surface 426 without a recess of another body section 422. The end 424 section is positioned adjacent a terminal one of the plurality of side-by-side body sections 422 to align the second surface 428 with the recess 432 of the terminal body section 422 with a surface of the end section 424. The abutment of recesses 432 with first surfaces 426 of the body sections 422 and the surface of the end section 424 forms the plurality of flow shafts 416 within the body 410.

The top member 412 of the cell culture assembly 402 includes a bottom surface 436 having a plurality of slots 438 extending from the bottom surface 436 into an interior of the top member 412. The plurality of slots 438 aligns with the plurality of flow shafts 416 of the body 410 and is constructed to receive ends of the plurality of slides 417 therein. The top member 412 defines a top bore 440 that is in fluid communication with the plurality of slots 438 that are in turn in fluid communication with the plurality of flow shafts 416. The top bore 440 includes a top opening 442 defined at an end surface 444 of the top member 412 for connection to a fluid flow path 446.

The bottom member 414 includes a top surface 448 having a plurality of slots 450 extending from the top surface 448 into an interior of the bottom member 414. The plurality of slots 450 aligns with the plurality of flow shafts 416 of the body 410 and is constructed to receive ends of the plurality of slides 417 therein. The bottom member 414 defines a bottom bore 452 that is in fluid communication with the plurality of slots 450 that are in turn in fluid communication with the plurality of flow shafts 416. The bottom bore 452 includes a bottom opening 454 defined at an end surface 456 of the bottom member 414 for connection to a fluid flow path 458.

The cell culture 402 assembly thereby is a flow chamber through which fluid may flow through one of either the top or bottom bore 440, 452, respectively, through the corresponding plurality of slots 438 or 450, through the flow shafts 416, through the other plurality of slots 438 or 450, and then through the other of either the top or bottom bore 440, 452 respectively. Cell cultures are placed on the plurality of slides 417 and positioned within the flow shafts 416. Cells cultured on the plurality of slides 417 are subject to shear stress when fluid flows through the flow chamber.

Figure 26:
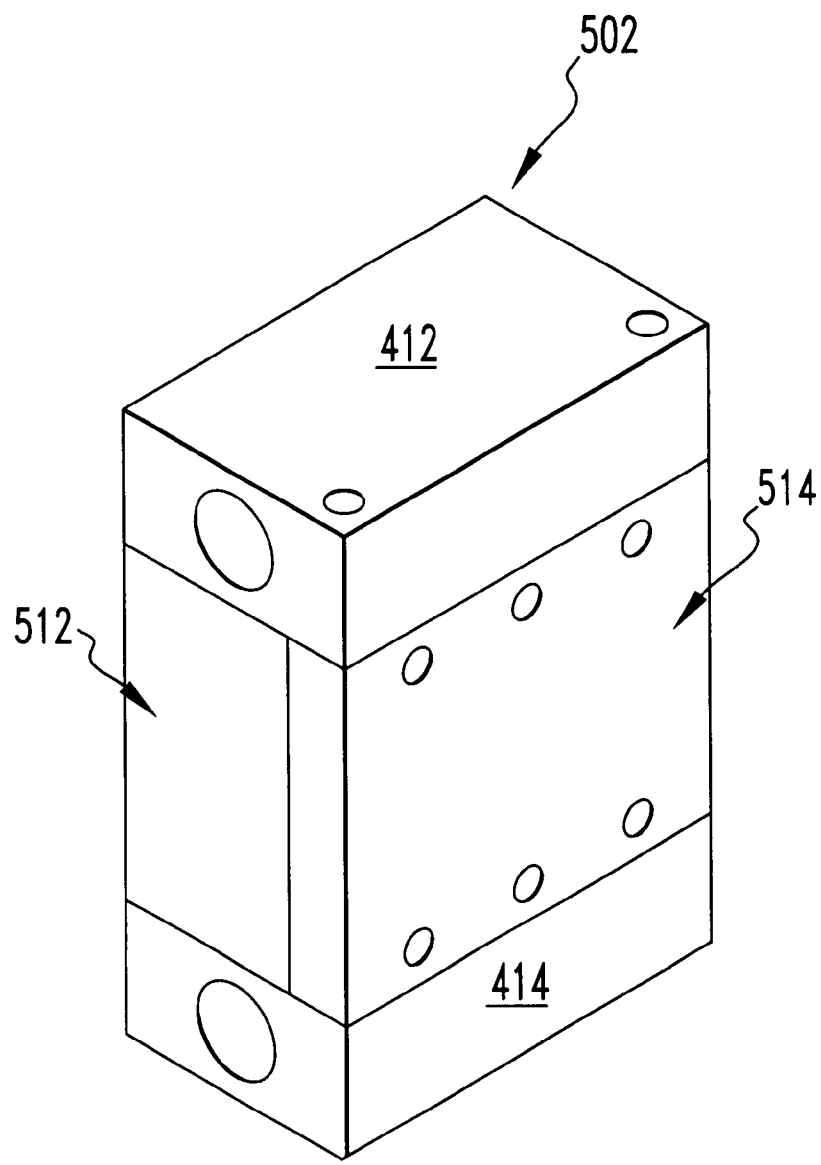
FIG. 26 is a perspective view of a two-piece, straight flow cell culture assembly made in accordance with the present invention including a body, a top member, and a bottom member.
Figure 27A:
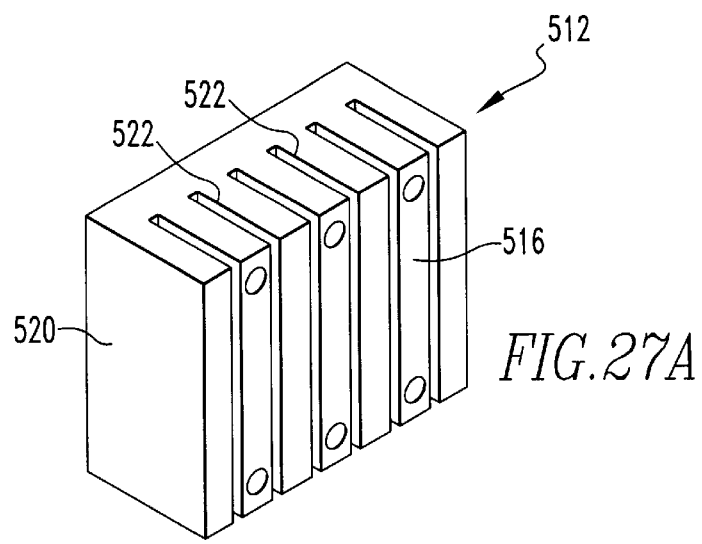
FIG. 27A is a perspective view of a first section of the body shown in FIG. 26.
Figure 27B:
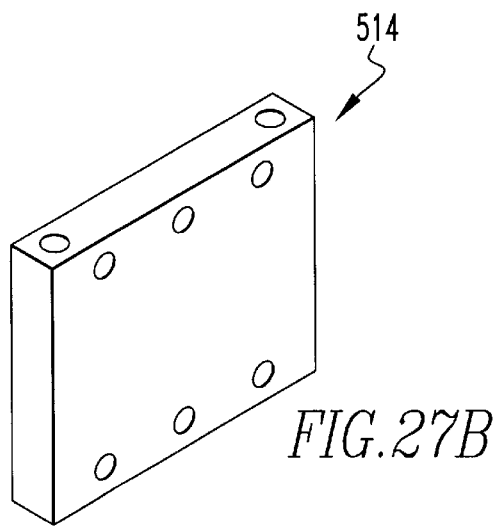
FIG. 27B is a perspective view of a second section of the body shown in FIG. 26.
Figure 27C:
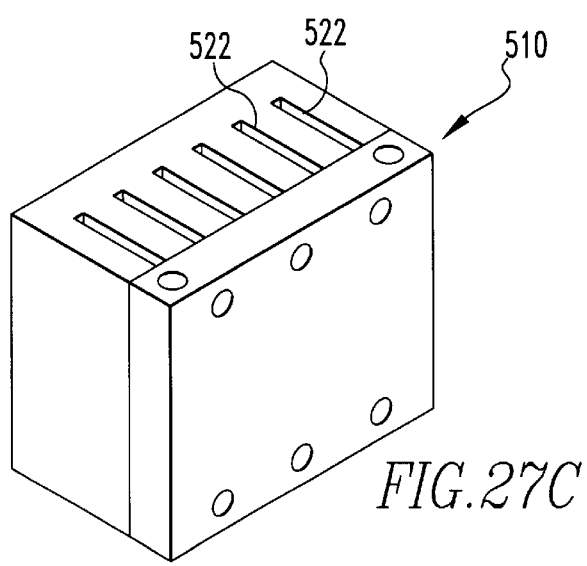
FIG. 27C is a perspective view of the body shown in FIG. 26.
Figure 28:
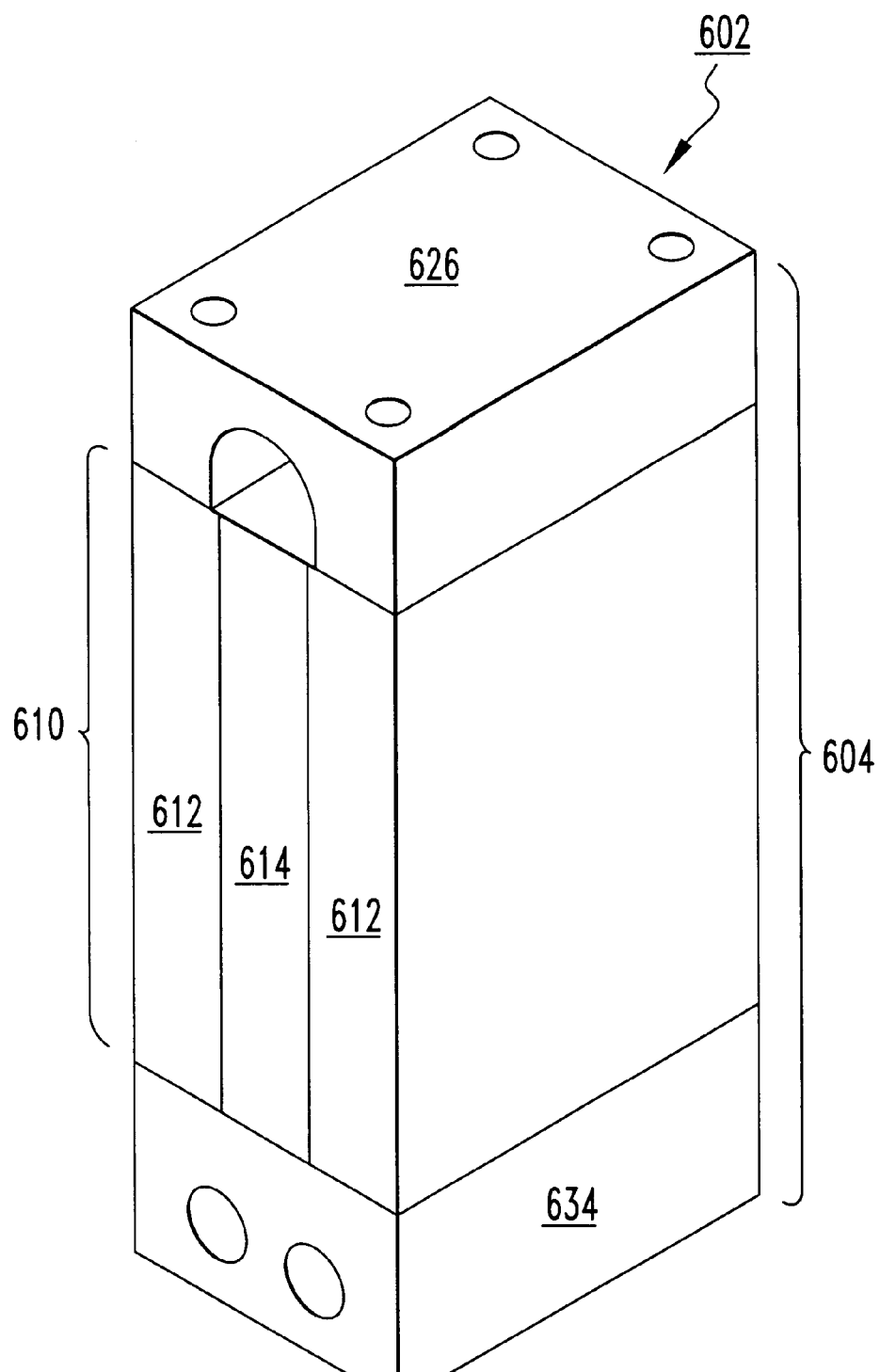
FIG. 28 is a perspective view of a serpentine flow cell culture assembly made in accordance with the present invention including a body, a top member, and a bottom member.
Figure 29A:
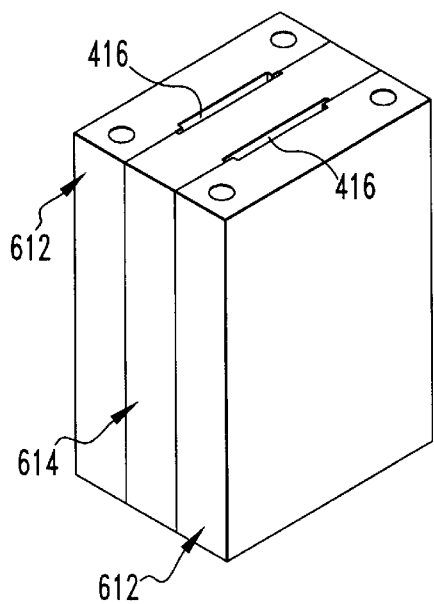
FIG. 29A is a perspective view of the body shown in FIG. 28.
Figure 29B:
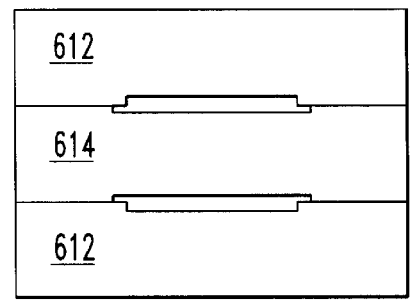
FIG. 29B is a top view of the body shown in FIG. 28.
Figure 29C:
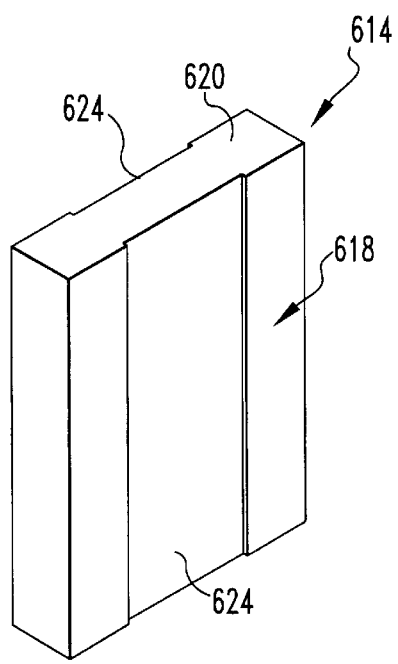
FIG. 29C is a perspective view of a body section of the body shown in FIG. 28.
Figure 29D:
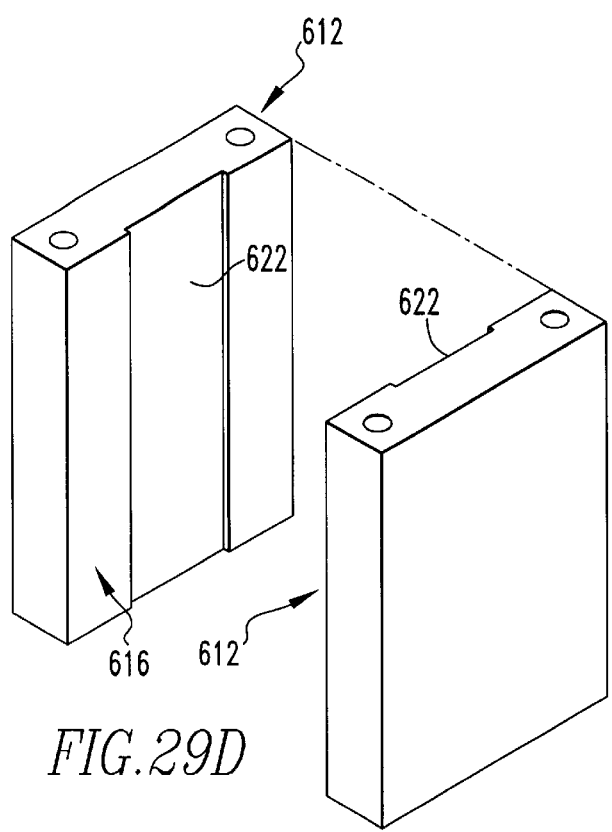
FIG. 29D is a perspective view of end sections of the body shown in FIG. 28.
Figure 30A:
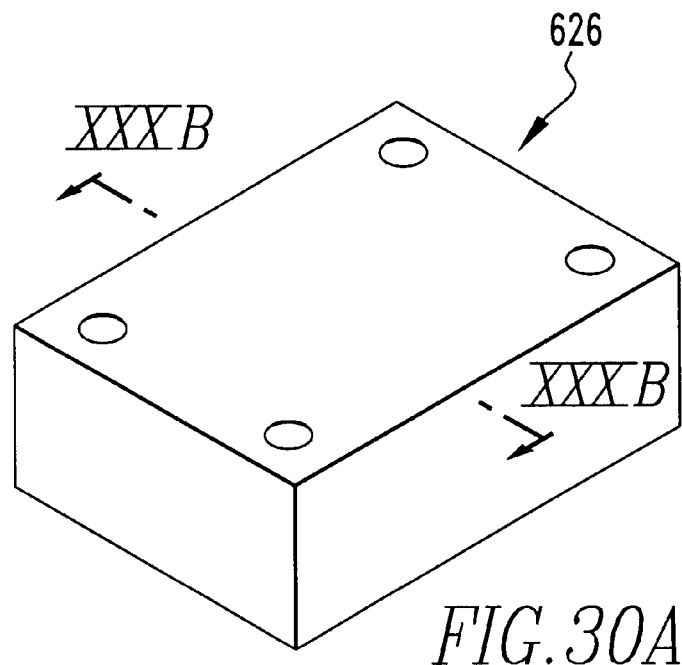
FIG. 30A is a perspective view of the top member shown in FIG. 28.
Figure 30B:
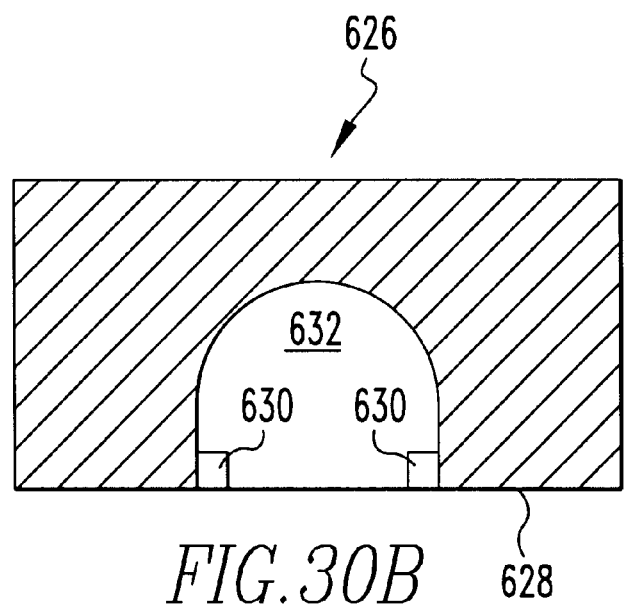
FIG. 30B is a cross-sectional end view taken along line XXXB—XXXB of the top member shown in FIG. 30A.
Figure 31A:
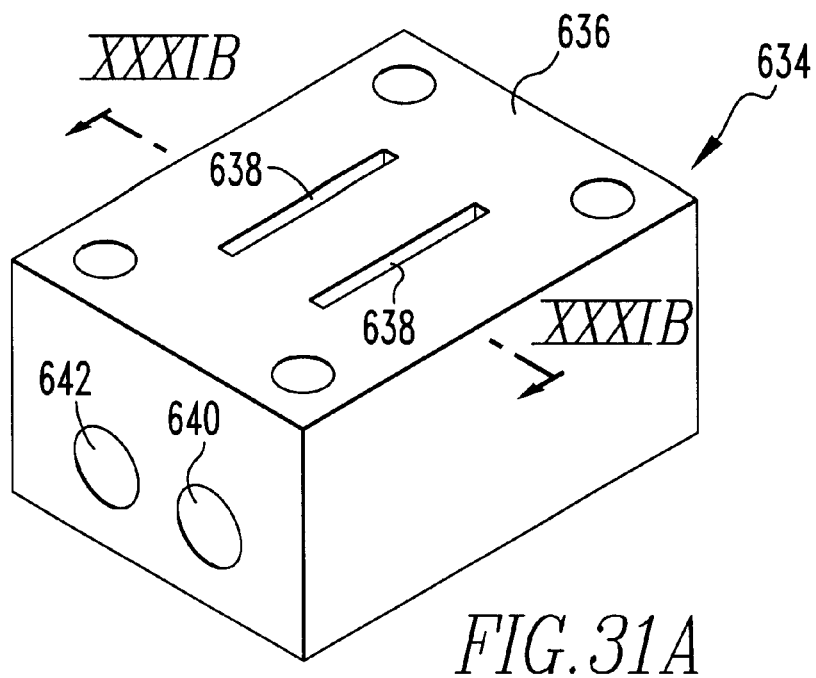
FIG. 31A is a perspective view of the bottom member shown in FIG. 28.
Figure 31B:
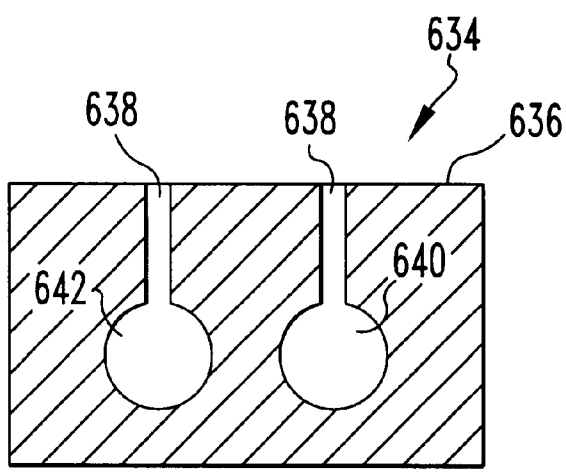
FIG. 31B is a cross-sectional end view taken along line XXXIB—XXXIB of the bottom member shown in FIG. 30A.
Figure 32:
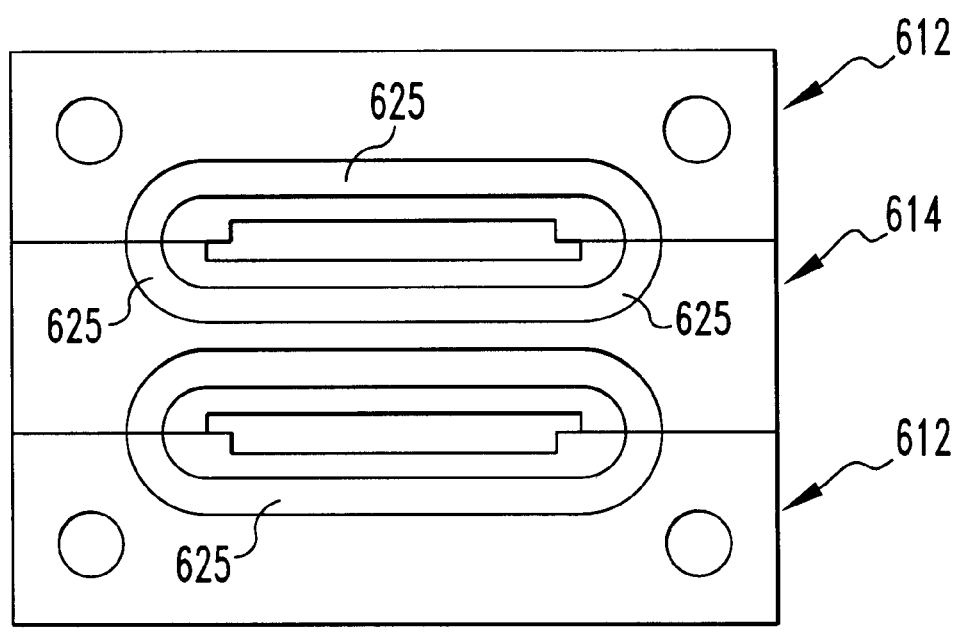
FIG. 32 is a top view of the body shown in FIG. 28 having O-ring slots.

Another variation of this embodiment is a two-section, straight flow cell culture assembly 502 as shown in FIGS. 26–27C. The body 510 has a first section 512 and a second section 514. The first section 512 includes a surface 516 and a plurality of substantially parallel slits 522 extending from the surface 516 into the interior of the first section 512 and for a length of the surface 516. The second section 514 mates with the first section 512 to close off the open slits 522 on the surface 516, thereby forming the plurality of flow shafts 416. The top member 412 and bottom member 414 are configured the same as discussed above with the multi-piece, straight flow cell culture assembly 402. This variation works in a similar manner as the multi-piece, straight flow cell culture assembly 402 as discussed above.

Another variation of this embodiment is a serpentine flow cell culture assembly 602 as shown in FIGS. 28–32. The assembly 602 includes a housing 604 having the plurality of flow shafts 416 therethrough. An inlet bore 640 is in fluid communication with a terminal flow shaft 416. An outlet bore 642 is in fluid communication with the other terminal flow shaft 416. A passageway 632 is in fluid communication with ends 420 of a pair of adjacent flow shafts 416 which are not in fluid communication with either bore 640 or 642.

The housing 604 preferably includes a body 610, a top member 626, and a bottom member 634. The body 610 includes opposed end sections 612 and at least one (preferably one) body section 614. The end and body sections 612, 614 respectively, are preferably generally rectangular in shape. Each end section 612 has a surface 616 defining a recess 622 that extends the length of the surface 616. The at least one body section 612 has opposed surfaces 618 having a recess 624 that extends the length of the surface 618. The at least one body section 614 is assembled in a parallel, side-by-side manner with the end sections 612 such that the recesses 622 of each end section 612 align with a recess 624 of the body section 614. The abutment of recesses 622 and 624 forms the plurality of flow shafts 420 within the body 610.

The end and body sections 612, 614, respectively, may include a plurality of O-ring grooves 625 that align to surround each end 420 of the plurality of flow shafts 416. O-rings (not shown) are placed in the O-ring grooves 625 to ensure a leakproof seal between the body 610 and the top member 626 and the bottom member 634 when assembled. Alternatively, O-ring grooves (not shown) may be located on the top member 626 and the bottom member 634 to surround each end 420 of the plurality of flow shafts 416 when the assembly 602 is assembled.

The top member 626 of the cell culture assembly 602 includes a surface 628 having a plurality of slots 630 that extend from the surface 628 into an interior of the top member 626. The plurality of slots 630 aligns with the plurality of flow shafts 416 of the body 610 and is constructed to receive ends of the plurality of slides 417 therein. The top member 626 defines at least one passageway 632 that provides fluid communication between adjacent ones of the plurality of slots 630 that are in turn in fluid communication with the plurality of flow shafts 416.

Figure 33A:
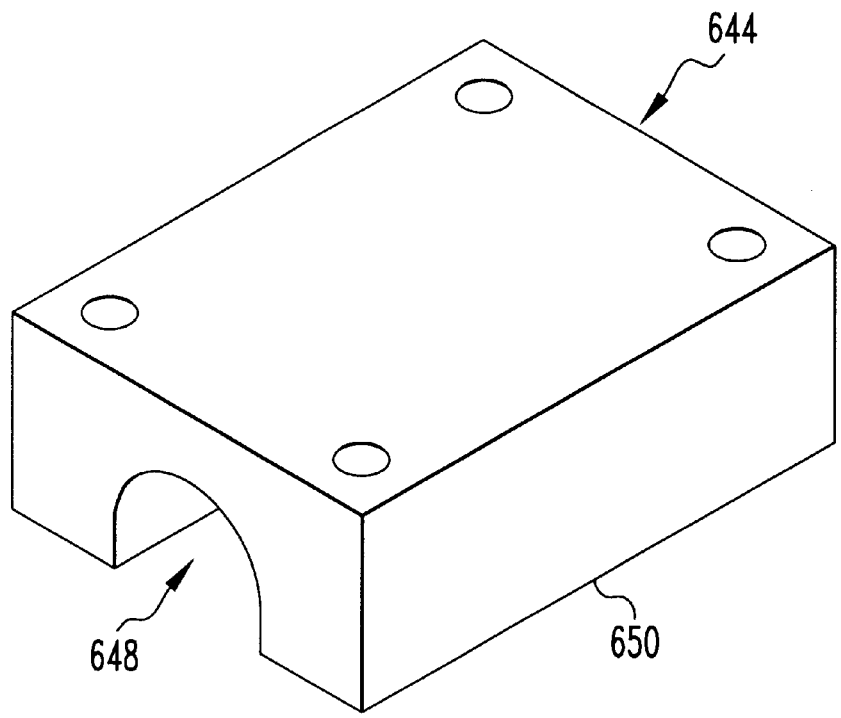
FIG. 33A is a perspective view of a head of the top member shown in FIG. 28.
Figure 33B:
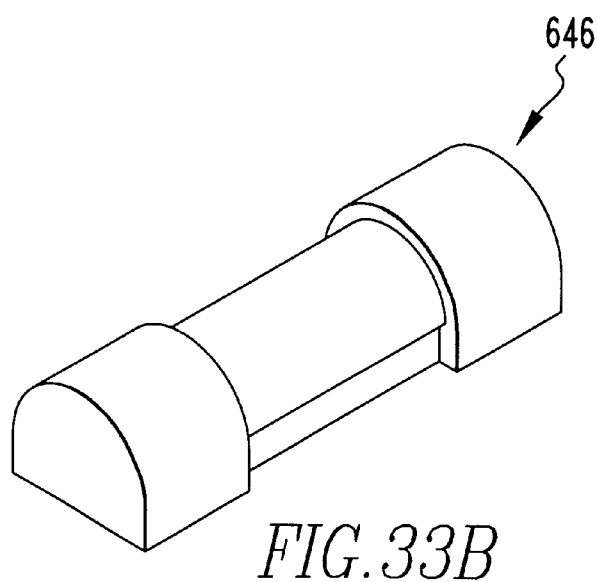
FIG. 33B is a perspective view of an insert of the top member shown in FIG. 28.

Alternatively, the top member 626 of the cell culture assembly 602 may include a head 644 and an insert 646, as shown in FIGS. 33A–33B. The head 644 includes a channel 648 that extends along a bottom surface 650 of the head 644. The insert 646 is configured to be removably inserted into the channel 648 such that once inserted, the insert 646 and the head 644 define the plurality of slots 630 and the passageway 632.

The bottom member 634 includes a surface 636 having a plurality of slots 638 that extend from the surface 636 into an interior of the bottom member 634. The plurality of slots 638 aligns with the plurality of flow shafts 416 of the body 610 and is constructed to receive ends of the plurality of slides 417 therein. The bottom member 634 further includes an inlet bore 640 and an outlet bore 642 for connection to a fluid flow path (not shown). The inlet bore 640 is in fluid communication with an end one of the plurality of slots 638 to provide a fluid path from the inlet bore 640 to an end one of the plurality of flow shafts 416. The outlet bore 642 is in fluid communication with an other end one of the plurality of slots 638 to provide a fluid path from an other end one of the plurality of flow shafts 416 to the outlet bore 642.

If more than one body section 614 is provided and the number of body sections 614 is odd (not shown), then the bottom member 634 further defines at least one passageway that provides fluid communication between adjacent ones of the plurality of slots 638 which are not in fluid communication with the bores 640 and 642. If more than one body section 614 is provided and the number of body sections 614 is even (not shown), then the bottom member 634 includes either an inlet bore 640 or an outlet bore 642, the top member 626 includes the other of the inlet bore 640 or the outlet bore 642, and the bottom member 63 further defines at least one passageway that provides fluid communication between adjacent ones of the plurality of slots 638. The passageways provide fluid communication between slots 638 that are not in fluid communication with either bore 640 or 642.

The cell culture assembly 602 thereby is a flow chamber through which fluid may flow. Cell cultures are placed on the plurality of slides 417 and positioned within the flow shafts 416. Cells cultured on the plurality of slides 417 are subject to shear stress when fluid flows through the flow chamber. In the preferred embodiment having one body section 614, fluid enters through the inlet bore 640 in the bottom member 634 and systematically traverses through the terminal slot 638 to the terminal flow shaft 416, through the terminal slot 630 in the top member 626, through the passageway 632 in the top member 626, through the other terminal slot 630 in the top member 626, through the other terminal flow shaft 416, through the other terminal slot 638 in the bottom member 634, and out the outlet bore 642 in the bottom member 634. The flow pattern is serpentine-like since it snakes through the bottom member 634, one flow shaft 416, the top member 626, the other flow shaft 416, and the bottom member 634. If more than one body section 614 is present, the flow pattern is still serpentine-like in that it snakes through adjacent flow shafts 416, via the top or bottom passageways, until the outlet bore 642 is reached.

In this variation of the cell culture assembly, a constant flow rate may be maintained since there is negligible pressure loss in the system. In other words, the pressure is constant from entry at the inlet bore 640 to exit at the outlet bore. In the other variation, pressure loss occurs due to a split in the flow path to the several flow shafts 416. Thus, higher fluid pressure must be used at the inlet bore 640.

It will be readily appreciated by those skilled in the art that modifications may be made to the invention without departing from the concepts disclosed in the foregoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

I claim:

1. A cell culture assembly for applying shear stress to cells, comprising:
   a body having a plurality of flow shafts therethrough, said plurality of flow shafts configured to removably receive a plurality of slides therein;
   a top member having a plurality of slots in alignment with and in fluid communication with said plurality of flow shafts, and a top bore extending from one end of said top member and in fluid communication with said plurality of slots; and
   a bottom member having a plurality of slots in alignment with and in fluid communication with said plurality of flow shafts, and a bottom bore extending from one end of said bottom member and in fluid communication with said plurality of slots.

2. The cell culture assembly as claimed in claim 1, wherein said body further includes:
   a plurality of O-ring grooves, one of said grooves surrounding each end of said plurality of flow shafts; and
   a plurality of O-rings removably insertable into said plurality of O-ring grooves.

3. The cell culture assembly as claimed in claim 1, wherein said body further includes:
   a plurality of body sections, each of said plurality of body sections having a first surface and a second surface defining a recess extending a length of said second surface,
   wherein said plurality of body sections is positioned adjacent each other such that said second surface of one of said body sections abuts said first surface of another of said body sections.

4. The cell culture assembly as claimed in claim 3, further including an end section having a surface positioned adjacent a second surface of a terminal one of said body sections.

5. The cell culture assembly as claimed in claim 4, wherein said plurality of body sections and said end section are generally rectangular.

6. A cell culture assembly for applying shear stress to cells, comprising:
   a body having a plurality of flow shafts therethrough, said plurality of flow shafts configured to removably receive a plurality of slides therein;
   a top member having a plurality of slots in alignment with and in fluid communication with said plurality of flow shafts, and a top bore extending from one end of said top member and in fluid communication with said plurality of slots; and
   a bottom member having a plurality of slots in alignment with and in fluid communication with said plurality of flow shafts, and a bottom bore extending from one end of said bottom member and in fluid communication with said plurality of slots,
   wherein said body further includes:
      a first section having a surface and a plurality of slits extending from said surface to an interior of said body and extending a length of said first section; and
      a second section abutting said surface of said first section thereby defining said plurality of flow shafts.

7. A cell culture assembly for applying shear stress to cells comprising:
   a housing having a top member, a bottom member, and a body defining a plurality of flow shafts therethrough, said flow shafts configured to removably receive a plurality of slides therein;
   an inlet in said top member or said bottom member in fluid communication with an end of a terminal one of said flow shafts;
   an outlet in said top member or said bottom member in fluid communication with an end of another terminal one of said flow shafts; and
   at least one passageway in said top member and/or said bottom member in fluid communication with ends of a pair of adjacent flow shafts, said ends of said adjacent flow shafts not being in fluid communication with said inlet and said outlet,
   wherein said body further includes:
      a pair of end sections, each of said end sections having a surface having a recess extending a length of said surface; and
      a body section having opposed surfaces, each opposed surface having a recess extending the length of said surface,
      wherein said body section is positioned between said end sections such that each said surface having said recess of said end sections opposes one of said recesses of said body sections thereby defining said flow shafts.

8. The cell culture assembly as claimed in claim 7, wherein said body further includes:

a plurality of O-ring grooves, one of said grooves surrounding each end of said plurality of flow shafts; and a plurality of O-rings removably insertable into said plurality of O-ring grooves.

9. The cell culture assembly as claimed in claim 7, further including a plurality of said body sections positioned between said end sections such that each said surface having said recess of said end sections opposes a terminal one of said body sections and each opposed surface of each said body section opposes another said opposed surface of another body section.

10. The cell culture assembly as claimed in claim 9, wherein said end sections and said body sections are generally rectangular.

11. The cell culture assembly as claimed in claim 7, wherein said end sections and said body sections are generally rectangular.

12. The cell culture assembly as claimed in claim 7, wherein said top member further includes a plurality of slots extending from a surface of said top member to said inlet, said outlet, and/or said at least one passageway and in fluid communication with said plurality of flow shafts and in fluid communication with said inlet, said outlet, and/or said at least one passageway.

13. The cell culture assembly as claimed in claim 12, wherein said top member further includes:

a head defining a channel extending along a bottom surface of said head; and an insert removably insertable into said channel thereby defining said plurality of slots and said passageway.

14. The cell culture assembly as claimed in claim 7, wherein said bottom member further includes a plurality of slots extending from a surface of said bottom member to said inlet, said outlet, and/or said at least one passageway and in fluid communication with said plurality of flow shafts and in fluid communication with said inlet, said outlet, and/or said at least one passageway.

15. The cell culture assembly as claimed in claim 14, wherein said top member further includes:

a head defining a channel extending along a bottom surface of said head; and an insert removably insertable into said channel thereby defining said plurality of slots and said passageway.

16. The cell culture assembly as claimed in claim 7, wherein:

said top member further includes a plurality of slots extending from a surface of said top member to said inlet, said outlet, and/or said at least one passageway and in fluid communication with said plurality of flow shafts and in fluid communication with said inlet, said outlet, and/or said at least one passageway; and said bottom member further includes a plurality of slots extending from a surface of said bottom member to said inlet, said outlet, and/or said at least one passageway and in fluid communication with said plurality of flow shafts and in fluid communication with said inlet, said outlet, and/or said at least one passageway.

17. The cell culture assembly as claimed in claim 16, wherein said top member further includes:

a head defining a channel extending along a bottom surface of said head; and an insert removably insertable into said channel thereby defining said plurality of slots and said passageway.

* * * * *